United States Patent
Takao et al.

(10) Patent No.: US 9,969,890 B2
(45) Date of Patent: May 15, 2018

(54) FLUORINATED ETHER COMPOUND, COMPOSITION FOR FORMING HARD COATING LAYER, AND ARTICLE HAVING HARD COATING LAYER

(71) Applicant: ASAHI GLASS COMPANY, LIMITED, Tokyo (JP)

(72) Inventors: Kiyotaka Takao, Tokyo (JP); Nobuyuki Otozawa, Tokyo (JP); Daisuke Jomuta, Tokyo (JP); Kuniko Okano, Tokyo (JP); Taiki Hoshino, Tokyo (JP)

(73) Assignee: Asahi Glass Company, Limited, Tokyo (JP)

( * ) Notice: Subject to any disclaimer, the term of this patent is extended or adjusted under 35 U.S.C. 154(b) by 203 days.

(21) Appl. No.: 14/821,941

(22) Filed: Aug. 10, 2015

(65) Prior Publication Data

US 2015/0344703 A1 Dec. 3, 2015

Related U.S. Application Data

(63) Continuation of application No. PCT/JP2014/055498, filed on Mar. 4, 2014.

(30) Foreign Application Priority Data

Mar. 5, 2013 (JP) .................................. 2013-043215
Mar. 5, 2013 (JP) .................................. 2013-043216

(51) Int. Cl.
| C07C 261/00 | (2006.01) |
|---|---|
| C09D 5/16 | (2006.01) |
| C09D 133/14 | (2006.01) |
| C07C 69/63 | (2006.01) |
| C07C 271/22 | (2006.01) |
| C07C 43/12 | (2006.01) |
| C09D 4/00 | (2006.01) |
| G02B 1/14 | (2015.01) |
| C08G 65/00 | (2006.01) |
| C08G 65/329 | (2006.01) |
| C09D 171/00 | (2006.01) |
| C08G 65/333 | (2006.01) |

(52) U.S. Cl.
CPC .............. *C09D 5/16* (2013.01); *C07C 43/126* (2013.01); *C07C 69/63* (2013.01); *C07C 271/22* (2013.01); *C08G 65/007* (2013.01); *C08G 65/329* (2013.01); *C08G 65/33348* (2013.01); *C09D 4/00* (2013.01); *C09D 133/14* (2013.01); *C09D 171/00* (2013.01); *G02B 1/14* (2015.01); *C08G 2650/48* (2013.01); *Y10T 428/3154* (2015.04)

(58) Field of Classification Search
CPC ..... C07C 271/22; C07C 43/126; C07C 69/63; C09D 133/14; C09D 4/00; C09D 5/16; C09D 171/00; G02B 1/14; C08G 2650/48; C08G 65/007; C08G 65/329; C08G 65/33348; C08G 65/48; Y10T 428/3154
See application file for complete search history.

(56) References Cited

U.S. PATENT DOCUMENTS 2,740,954 A * 4/1956 Kleefeld ................. H01J 29/89
313/478
2010/0304113 A1* 12/2010 Chang ..................... B82Y 30/00
428/220

FOREIGN PATENT DOCUMENTS

| EP | 2 982 702 A1 | 2/2016 |
|---|---|---|
| JP | 2931599 | 8/1999 |
| JP | 3963169 | 8/2007 |
| JP | 4547642 | 9/2010 |
| JP | 4923572 | 4/2012 |
| WO | WO 00/56694 | 9/2000 |
| WO | WO 2003/002628 | 1/2003 |
| WO | WO 2004/044062 | 5/2004 |
| WO | WO 2009/133770 | 11/2009 |
| WO | WO 2013/121984 | 8/2013 |
| WO | WO 2013/121985 | 8/2013 |
| WO | WO 2013/121986 | 8/2013 |

OTHER PUBLICATIONS

International Search Report dated Jun. 10, 2014 in PCT/JP2014/055498 filed Mar. 4, 2014.

* cited by examiner

*Primary Examiner* — Yevgeny Valenrod
*Assistant Examiner* — Blaine G Doletski
(74) *Attorney, Agent, or Firm* — Oblon, McClelland, Maier & Neustadt, L.L.P.

(57) ABSTRACT

Provided is a fluorinated ether compound capable of imparting excellent antifouling properties such as oil-based ink repellency, fingerprint stain removability, to a hard coating layer; a composition for forming a hard coating layer, and an article having an antifouling hard coating layer formed from the composition. The fluorinated ether compound has either a poly(oxyperfluoroalkylene) chain having a repeated unit that includes a $C_{1-2}$ oxyperfluoroalkylene group and a $C_{3-6}$ oxyperfluoroalkylene group, bonded to each other, or a poly(oxyperfluoroalkylene) chain having a repeated unit that contains a $C_4$ oxyperfluoroalkylene group and a different oxyperfluoroalkylene group, bonded to each other, a linking group bonded to a first terminal of the poly(oxyperfluoroalkylene) chain, and at least one (meth)acryloyl group bonded to the linking group.

17 Claims, No Drawings

FLUORINATED ETHER COMPOUND, COMPOSITION FOR FORMING HARD COATING LAYER, AND ARTICLE HAVING HARD COATING LAYER

TECHNICAL FIELD

The present invention relates to a fluorinated ether compound capable of imparting excellent antifouling properties to an object (such as a hard coating layer), a photo-curable composition for forming a hard coating layer, which contains such a compound, and an article having an antifouling hard coating layer formed of such a composition.

BACKGROUND ART

Various articles which are required to have abrasion resistance (such as optical articles, displays, optical recording media, etc.) usually have, on their surface, a hard coating layer to prevent scratching, etc.

Further, such articles are desired to have properties to prevent fouling (such as fingerprints, sebum, sweat, cosmetics, foods, oil-based ink, etc.) from attaching to their surface, or to readily remove such fouling if attached to their surface. For example, if fouling attaches to the surface of an eye glass lens, good visibility tends to be impaired, and its visual appearance tends to be poor. If fouling attaches to the surface of an optical recording medium, a trouble may be thereby caused in recording or reproduction of a signal. If fouling attaches to the surface of a display, the visibility tends to be thereby deteriorated, and in the case of a display with a touch panel, the operation efficiency tends to be thereby adversely affected.

As fluorinated ether compounds capable of imparting antifouling properties to hard coating layers, the following ones have been proposed.

(1) A compound having a hydroxy group and a poly(oxyperfluoroalkylene) chain having $C_{1-3}$ oxyperfluoroalkylene units, and a fluorinated ether compound having a (meth)acryloyl group, which is obtained by reacting a compound having a hydroxy group and a (meth)acryloyl group, with a triisocyanate (Patent Document 1).

(2) A copolymer which has a unit having a poly(oxyperfluoroalkylene) chain having $C_{1-3}$ oxyperfluoroalkylene units, and a unit having a (meth)acryloyl group (Patent Document 2).

PRIOR ART DOCUMENTS

Patent Documents

Patent Document 1: Japanese Patent No. 3,963,169
Patent Document 2: Japanese Patent No. 4,547,642

DISCLOSURE OF INVENTION

Technical Problem

However, according to a finding by the present inventors, the fluorinated ether compound in (1) and the copolymer in (2) are inadequate in the properties for repelling oil-based ink (hereinafter referred to as oil-based ink repellency) while they have good fingerprint stain removability among the antifouling properties.

It is an object of the present invention to provide a fluorinated ether compound capable of imparting excellent antifouling properties (oil-based ink repellency, fingerprint stain removability) to an object (such as a hard coating layer), a composition for forming a hard coating layer, capable of forming a hard coating layer having good abrasion resistance and antifouling properties (oil-based ink repellency, fingerprint stain removability), and an article having a hard coating layer excellent in abrasion resistance and antifouling properties (oil-based ink repellency, fingerprint stain removability).

Solution to Problem

The present invention provides a fluorinated ether compound, a composition for forming a hard coating layer, and an article having a hard coating layer, which have the following constructions [1] to [15].

[1] A fluorinated ether compound which has
either a poly(oxyperfluoroalkylene) chain having a unit repeated that comprises a group constituted by one to three of at least one type of a $C_{1-2}$ oxyperfluoroalkylene group and a group constituted by one to three of at least one type of a $C_{3-6}$ oxyperfluoroalkylene group, bonded to each other, or a poly(oxyperfluoroalkylene) chain having a unit repeated that comprises a $C_4$ oxyperfluoroalkylene group and an oxyperfluoroalkylene group other than such a group, bonded to each other,
a linking group bonded to a first terminal of the above poly(oxyperfluoroalkylene) chain, and
at least one (meth)acryloyl group bonded to the above linking group.

[2] The fluorinated ether compound according to [1], wherein the above poly(oxyperfluoroalkylene) chain is a poly(oxyperfluoroalkylene) chain having a unit repeated that comprises a $C_2$ oxyperfluoroalkylene group and a group constituted by one to three of at least one type of a $C_{3-6}$ oxyperfluoroalkylene group, bonded to each other, or a poly(oxyperfluoroalkylene) chain having a unit repeated that comprises a $C_4$ oxyperfluoroalkylene group and a $C_2$ oxyperfluoroalkylene group, bonded to each other.

[3] The fluorinated ether compound according to [1] or [2], wherein the above poly(oxyperfluoroalkylene) chain is a poly(oxyperfluoroalkylene) chain having a unit repeated that comprises an oxyperfluorodimethylene group and an oxyperfluorotetramethylene group, bonded to each other.

[4] The fluorinated ether compound according to any one of [1] to [3], wherein at a second terminal of the above poly(oxyperfluoroalkylene) chain, a $C_{1-6}$ perfluoroalkoxy group is bonded in a case where the second terminal atom is a carbon atom, or a $C_{1-6}$ perfluoroalkyl group is bonded in a case where the second terminal atom is an oxygen atom.

[5] The fluorinated ether compound according to [4], wherein the second terminal of the above poly(oxyperfluoroalkylene) chain is at the side where the $C_2$ oxyperfluoroalkylene group is present.

[6] The fluorinated ether compound according to any one of [1] to [5], which has a number average molecular weight of from 2,000 to 40,000.

[7] A fluorinated ether compound represented by the following formula (1):

$$A-O-[R^{f1}O-R^{f2}O]_n-B \qquad (1)$$

provided that symbols in the formula (1) are as follows:
n: an integer of at least 2,
$R^{f1}$: a perfluorodimethylene group,
$R^{f2}$: a $C_{3-18}$ perfluoroalkylene group which may have an etheric oxygen atom between carbon atoms, A: a $C_{1-6}$ perfluoroalkyl group, a $C_{2-6}$ perfluoroalkyl group having an etheric oxygen atom, or B, B: a group represented by the following formula (2):

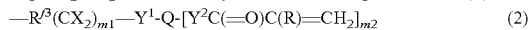
$$—R^{f3}(CX_2)_{m1}—Y^1-Q-[Y^2C(=O)C(R)=CH_2]_{m2} \quad (2)$$

provided that symbols in the formula (2) are as follows:

$R^{f3}$: a $C_{1-20}$ perfluoroalkylene group which may have an etheric oxygen atom between carbon atoms, X: a hydrogen atom or a fluorine atom, m1: 0 or 1, $Y^1$: a single bond, —C(=O)NH— (provided that Q is bonded to N), —OC(=O)NH— (provided that Q is bonded to N), —O—, —C(=O)O— (provided that Q is bonded to O), —OC(=O)O—, —NHC(=O)NH— or —NHC(=O)O— (provided that Q is bonded to O), Q: a single bond or a (m2+1) valent organic group, $Y^2$: —O—, —NH— or —NHC(=O)O—$(C_kH_{2k})$—O— (provided that k is an integer of from 1 to 10, and Q is bonded to N), R: a hydrogen atom or a methyl group, m2: an integer of at least 1, provided that in the formula (2), when m1 is 0, $Y^1$ is not —O—, —OC(=O)NH— or —OC(=O)—, when $Y^1$ is —C(=O)NH—, —OC(=O)NH—, —O—, —C(=O)O—, —OC(=O)O—, —NHC(=O)NH— or —NHC(=O)O—, Q is a (m2+1) valent organic group, and when each of $Y^1$ and $Y^2$ is —O—, Q is not a single bond.

[8] The fluorinated ether compound according to [7], wherein the above $R^{f2}$ is a perfluorotetramethylene group, and the above B is —$CF_2CF_2OCF_2CF_2CF_2CH_2$—OC(=O)C(R)=$CH_2$.

[9] The fluorinated ether compound according to [7], wherein the above $R^{f2}$ is a perfluorotetramethylene group, and the above B is —$CF_2CF_2OCF_2CF_2CF_2CH_2$—O—C(=O)NH-Q-[NHC(=O)O—$(C_kH_{2k})$—O—C(=O)C(R)=$CH_2$]m2 (where m2 is 1 or 2, provided that when m2 is 1, Q is a bivalent group obtained by removing two isocyanate groups from a diisocyanate compound, and when m2 is 2, Q is a trivalent group obtained by removing three isocyanate groups from a triisocyanate compound, and k is an integer of from 2 to 6).

[10] A compound represented by the following formula:

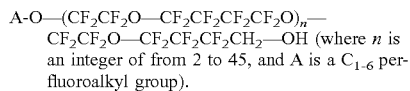
A-O—$(CF_2CF_2O—CF_2CF_2CF_2CF_2O)_n$— $CF_2CF_2O—CF_2CF_2CF_2CH_2$—OH (where n is an integer of from 2 to 45, and A is a $C_{1-6}$ perfluoroalkyl group).

[11] A composition for forming a hard coating layer, which comprises the fluorinated ether compound as defined in any one of [1] to [9], a photopolymerizable compound (provided that the above fluorinated ether compound is excluded) and a photopolymerization initiator.

[12] The composition for forming a hard coating layer according to [11], wherein the content of the above fluorinated ether compound is from 0.01 to 5 mass % in the solid content (100 mass %).

[13] The composition for forming a hard coating layer according to [11] or [12], which further contains a medium.

[14] An article comprising a substrate and a hard coating layer formed from the composition for forming a hard coating layer as defined in any one of [11] to [13].

[15] The article according to [14], wherein the material for the substrate is a metal, a resin, glass, ceramics or a composite material thereof.

Advantageous Effects of Invention

The fluorinated ether compound of the present invention is capable of imparting excellent antifouling properties (oil-based ink repellency, fingerprint stain removability) to an object (such as a hard coating layer).

The composition for forming a hard coating layer of the present invention is capable of forming a hard coating layer excellent in abrasion resistance and antifouling properties (oil-based ink repellency, fingerprint stain removability).

The article of the present invention has a hard coating layer excellent in abrasion resistance and antifouling properties (oil-based ink repellency, fingerprint stain removability).

DESCRIPTION OF EMBODIMENTS

In this specification, a compound represented by the formula (1) will be referred to as a compound (1). Compounds represented by other formulae will be referred to in the same manner.

The following definitions of terms shall apply to this specification and claims.

A (meth)acryloyl group is meant for the after-described —C(=O)C(R)=$CH_2$ group and is a generic term for an acryloyl group and a methacryloyl group.

A (meth)acrylate is a generic term for an acrylate and a methacrylate.

A polymerizable monomer is a compound having a polymerization-reactive carbon-carbon double bond.

An etheric oxygen atom is an oxygen atom to form an ether bond (—O—) between carbon-carbon atoms.

A linking group is a group to link a poly(oxyperfluoroalkylene) chain and a (meth)acryloyl group, and is, for example, a group having —C(=O)C(R)=$CH_2$ group excluded from B in the after-described formula (1). Such a group itself may have other oxyperfluoroalkylene group not belonging to the above poly(oxyperfluoroalkylene) chain.

An organic group is a group having carbon atoms.

[Fluorinated Ether Compound]

The fluorinated ether compound of the present invention (hereinafter referred to also as the present compound) is a compound which has either a poly(oxyperfluoroalkylene) chain having a unit repeated that comprises a group constituted by one to three of at least one type of a $C_{1-2}$ oxyperfluoroalkylene group and a group constituted by one to three of at least one type of a $C_{3-6}$ oxyperfluoroalkylene group, bonded to each other (hereinafter referred to also as the first embodiment), or a poly(oxyperfluoroalkylene) chain having a unit repeated that comprises a $C_4$ oxyperfluoroalkylene group and an oxyperfluoroalkylene group other than such a group, bonded to each other (hereinafter referred to also as the second embodiment), a linking group bonded to a first terminal of the poly(oxyperfluoroalkylene) chain, and at least one (meth)acryloyl group bonded to the linking group.

The present compound may have other oxyperfluoroalkylene group not belonging to the above poly(oxyperfluoroalkylene) chain.

The present compound may have a linking group only at the first terminal of the poly(oxyperfluoroalkylene) chain, or may have linking groups at both terminals (i.e. at the first terminal and the second terminal) of the poly(oxyperfluoroalkylene) chain. It preferably has a linking group only at the first terminal of the poly(oxyperfluoroalkylene) chain, from such a viewpoint that in the hard coating layer, a terminal group bonded to the second terminal of the poly(oxyperfluoroalkylene) chain becomes a free terminal to impart antifouling properties (oil-based ink repellency, fingerprint stain removability) to the hard coating layer.

The present compound may be a single compound, or a mixture of two or more types different in the poly(oxyperfluoroalkylene) chain, the terminal group, the linking group, etc.

One (the first embodiment) of the above two types of poly(oxyperfluoroalkylene) chain is composed of repetition of a unit that comprises a group constituted by one to three of at least one type of a $C_{1-2}$ oxyperfluoroalkylene group and a group constituted by one to three of at least one type of a $C_{3-6}$ oxyperfluoroalkylene group, bonded to each other.

Said group constituted by one to three of at least one type of a $C_{1-2}$ oxyperfluoroalkylene group, may be constituted solely by one type of oxyperfluoroalkylene units having the same number of carbon atoms, or may be constituted by two types of oxyperfluoroalkylene units different in the number of carbon atoms. Such a group constituted by at least one type of a $C_{1-2}$ oxyperfluoroalkylene group, is preferably a group constituted by one to three of a $C_2$ peroxyalkylene group. Such a $C_2$ peroxyalkylene group is preferably an oxyperfluorodimethylene group ($CF_2CF_2O$) as a linear peroxyalkylene group.

Said group constituted by one to three of at least one type of a $C_{3-6}$ oxyperfluoroalkylene group, may be constituted solely by one type of oxyperfluoroalkylene units having the same number of carbon atoms, or may be constituted by two or more types of oxyperfluoroalkylene units different in the number of carbon atoms.

With a view to sufficiently imparting oil-based ink repellency to the hard coating layer, such a group constituted by one to three of at least one type of a $C_{3-6}$ oxyperfluoroalkylene group, is preferably one having a $C_4$ oxyperfluoroalkylene group, and preferably one having ($CF_2CF_2CF_2CF_2O$).

When the present compound has a group constituted by one to three of at least one type of a $C_{1-2}$ oxyperfluoroalkylene group, it is capable of imparting fingerprint stain removability to the hard coating layer. And, when it has a group constituted by one to three of at least one type of a $C_{3-6}$ oxyperfluoroalkylene group, it is capable of imparting oil-based ink repellency to the hard coating layer. The poly(oxyperfluoroalkylene) chain is composed by repetition of a unit wherein the above two types of groups are bonded to each other. In repetition of the unit, the above two types of groups may be arranged in any of random, block or alternate form, but they are preferably arranged alternately. When the above two types of groups are alternately arranged, both of the properties attributable to a group constituted by one to three of at least one type of a $C_{1-2}$ oxyperfluoroalkylene group, and the properties attributable to a group constituted by one to three of at least one type of a $C_{3-6}$ oxyperfluoroalkylene group, can effectively be obtained. That is, the hard coating layer will be excellent not only in antifouling properties (oil-based ink repellency, fingerprint stain removability) but also in abrasion resistance.

The other (the second embodiment) of the above two types of poly(oxyperfluoroalkylene) chain is composed of repetition of a unit that comprises a $C_4$ oxyperfluoroalkylene group and an oxyperfluoroalkylene group other than such a group, bonded to each other.

The $C_4$ oxyperfluoroalkylene group may be a branched oxyperfluoroalkylene group, but is preferably an oxyperfluorotetramethylene group ($CF_2CF_2CF_2CF_2O$) as a linear oxyperfluoroalkylene group.

Another oxyperfluoroalkylene group is preferably a linear or branched oxyperfluoroalkylene group having 1, 2, 3, 5 or 6 carbon atoms, particularly preferably a $C_2$ peroxyalkylene group. The $C_2$ peroxyalkylene group is preferably an oxyperfluorodimethylene group ($CF_2CF_2O$) as a linear peroxyalkylene group. All units in the poly(oxyperfluoroalkylene) chain may be the same, or part of units may be different from other units. Two units being different means that oxyperfluoroalkylene groups other than the $C_4$ oxyperfluoroalkylene group are different.

When the present compound has the $C_4$ oxyperfluoroalkylene group, the hard coating layer will be excellent in oil-based ink repellency. However, a poly(oxyperfluoroalkylene) chain composed solely of the $C_4$ oxyperfluoroalkylene group has high crystallinity, whereby the fingerprint stain removability tends to be inadequate. By incorporating another oxyperfluoroalkylene group, the crystallinity of the poly(oxyperfluoroalkylene) chain will be lowered, and the hard coating layer will be excellent in oil-based ink repellency and fingerprint stain removability.

In the poly(oxyperfluoroalkylene) chain, the $C_4$ oxyperfluoroalkylene group and another oxyperfluoroalkylene group may be arranged in any of random, block or alternate form, but they are preferably arranged alternatively. When they are alternatively arranged, the hard coating layer will be excellent not only in antifouling properties (oil-based ink repellency, fingerprint stain removability), but also in abrasion resistance.

Also in a block form, it is preferred to have a linking group only at the first terminal of the poly(oxyperfluoroalkylene) chain. In such a case, when the side close to the perfluoroalkyl group is a perfluoroalkylene group having a less number of carbon atoms, and the side close to the (meth)acryloyl group is a perfluoroalkylene group having a larger number of carbon atoms, the hard coating layer will be further improved in antifouling properties (oil-based ink repellency, fingerprint stain removability). For example, it is preferred that the side close to the perfluoroalkyl group is a block of $C_{1-3}$ oxyperfluoroalkylene groups, and the side close to the (meth)acryloyl group is a block of $C_{4-15}$ oxyperfluoroalkylene groups, which essentially contains a $C_4$ oxyperfluoroalkylene group.

In the above two types of poly(oxyperfluoroalkylene) chain, the poly(oxyperfluoroalkylene) chain of the first embodiment is preferably a poly(oxyperfluoroalkylene) chain having a unit repeated that comprises a $C_2$ oxyperfluoroalkylene group and a group constituted by one to three of at least one type of a $C_{3-6}$ oxyperfluoroalkylene group, bonded to each other. Particularly preferred among them, is a poly(oxyperfluoroalkylene) chain having a unit repeated that comprises an oxyperfluorodimethylene group and an oxyperfluorotetramethylene group, bonded to each other.

In the above two types of poly(oxyperfluoroalkylene) chain, the poly(oxyperfluoroalkylene) chain of the second embodiment is preferably a poly(oxyperfluoroalkylene) chain having a unit repeated that comprises a $C_4$ oxyperfluoroalkylene group and a $C_2$ oxyperfluoroalkylene group, bonded to each other. Particularly preferred among them, is a poly(oxyperfluoroalkylene) chain having a unit repeated that comprises an oxyperfluorotetramethylene group and an oxyperfluorodimethylene group, bonded to each other.

Hereinafter, the above two types of poly(oxyperfluoroalkylene) chain will be collectively referred to simply as a poly(oxyperfluoroalkylene) chain.

The poly(oxyperfluoroalkylene) chain having a unit repeated that comprises an oxyperfluorodimethylene group and an oxyperfluoroalkylene group having at least 3 carbon atoms (which may have an etheric oxygen atom between carbon atoms), bonded to each other, can be produced by a known method as disclosed in U.S. Pat. No. 5,134,211. By this known method, a compound having a poly(oxypolyfluoroalkylene) chain having hydrogen atoms can be produced. By converting the hydrogen atoms in the poly (oxypolyfluoroalkylene) chain of the compound obtained by this known method, to fluorine atoms, a poly(oxyperfluoroalkylene) chain can be obtained.

That is, in the above known method, by a polyaddition reaction of "$CF_2=CFOR^4CF_2CH_2OH$", a compound having a poly(oxypolyfluoroalkylene) chain composed of repetition of "$[CF_2CFHOR^4CF_2CH_2O]$" can be produced (the above "$R^4$" is, for example, a perfluoroalkylene group or "$[CF_2CF(CF_3)O]_n(CF_2)_m$"). Therefore, then, by fluorinating "$[CF_2CFHOR^4CF_2CH_2O]$", a poly(oxyperfluoroalkylene) chain having "$[CF_2CF_2OR^4CF_2CF_2O]$" units can be obtained. For the substitution of hydrogen atoms by fluorine atoms, it is preferred to employ a direct fluorination method using elemental fluorine.

Thus, the poly(oxyperfluoroalkylene) chain in the present invention is preferably a poly(oxyperfluoroalkylene) chain which can be produced by the above method.

In the above known method, at the time of producing the compound having a poly(oxypolyfluoroalkylene) chain composed of repetition of "$[CF_2CFHOR^4CF_2CH_2O]$" by a polyaddition reaction of "$CF_2=CFOR^4CF_2CH_2OH$", if an alkanol or a polyfluoroalkanol is used as an initiator, a compound having an alkoxy group or a polyfluoroalkoxy group bonded to a terminal carbon atom at the $CF_2CFHO$ side of the poly(oxypolyfluoroalkylene) chain will be formed. Therefore, by fluorinating a compound having a poly(oxypolyfluoroalkylene) chain having an alkoxy group or a polyfluoroalkoxy group bonded, it is possible to form a poly(oxypolyfluoroalkylene) chain having a perfluoroalkoxy group bonded to a carbon atom of the terminal oxyperfluorodimethylene group. By using an alkanol or a polyfluoroalkanol having an etheric oxygen atom, instead of the alkoxy group or the polyfluoroalkoxy group, a perfluoroalkoxy group having an etheric oxygen atom can be formed in the same manner.

The present compound is preferably a compound having a $C_{1-6}$ perfluoroalkyl group or a $C_{2-6}$ perfluoroalkyl group having an etheric oxygen atom, bonded at the second terminal of the poly(oxyperfluoroalkylene) chain, particularly preferably a compound having a $C_{1-6}$ perfluoroalkyl group bonded. The bonds at the two terminals of the poly(oxyperfluoroalkylene) chain, are a bond of a carbon atom and a bond of an oxygen atom. Therefore, each of the above perfluoroalkyl group and the above perfluoroalkyl group having an etheric oxygen atom will be bonded via an oxygen atom in a case where the second terminal is at the side of the bond of a carbon atom, or will be directly bonded in a case where the second terminal is at the side of the bond of an oxygen atom. That is, in a case where the second terminal is at the side of the bond of a carbon atom, a $C_{1-6}$ perfluoroalkoxy group or a $C_{2-6}$ perfluoroalkoxy group having an etheric oxygen atom, will be bonded to the second terminal.

By such a construction, it is possible to impart excellent antifouling properties (oil-based ink repellency, fingerprint stain removability) to the hard coating layer. As the perfluoroalkyl group, $CF_3$— or $CF_3CF_2$— is particularly preferred.

The present compound is preferably a compound wherein in the (oxyperfluoroalkylene) chain, in the first embodiment, the side close to the perfluoroalkyl group is a group constituted by one to three of at least one type of a $C_{1-2}$ oxyperfluoroalkylene group, and the side close to the (meth) acryloyl group is a group constituted by one to three of at least one type of a $C_{3-6}$ oxyperfluoroalkylene group. Particularly preferred is a compound wherein the side close to the perfluoroalkyl group is an oxyperfluorodimethylene group, and the side close to the (meth)acryloyl group is the other oxyperfluoroalkylene group.

In the (oxyperfluoroalkylene) chain, in the second embodiment, a compound is preferred wherein the side close to the perfluoroalkyl group is an oxyperfluoroalkylene group other than a $C_4$ oxyperfluoroalkylene group, and the side close to the (meth)acryloyl group is a $C_4$ oxyperfluoroalkylene group. Particularly preferred is a compound wherein the side close to the perfluoroalkyl group is an oxyperfluorodimethylene group, and the side close to the (meth)acryloyl group is a $C_4$ oxyperfluoroalkylene group.

By such a construction, the hard coating layer will be excellent in antifouling properties (oil-based ink repellency, fingerprint stain removability). The reason is considered to be such that a highly flexible oxyperfluorodimethylene group can be present at the side close to a perfluoroalkyl group as a free terminal, whereby the mobility of the perfluoroalkyl group tends to be high.

The number average molecular weight of the present compound is preferably from 2,000 to 40,000. When the number average molecular weight is within such a range, it is excellent in compatibility with other components in the composition for forming a hard coating layer. The number average molecular weight of the present compound is more preferably from 2,100 to 10,000, particularly preferably from 2,400 to 6,000.

The present compound has a poly(oxyperfluoroalkylene) chain, and therefore, the content of fluorine atoms is large. Further, as mentioned above, an oxyperfluoroalkylene group having a small number of carbon atoms (particularly an oxyperfluorodimethylene group) to decrease crystallinity of the poly(oxyperfluoroalkylene) chain and to impart fingerprint stain removability to the hard coating layer, and an oxyperfluoroalkylene group having a large number of carbon atoms (particularly an oxyperfluorotetramethylene group) to impart oil-based ink repellency to the hard coating layer, are linked so that they are alternately arranged. Therefore, the present compound is capable of imparting excellent antifouling properties (oil-based ink repellency, fingerprint stain removability) to the hard coating layer.

(Compound (1))

As a compound according to the first embodiment, the present compound is preferably a compound represented by the following formula (1) (hereinafter referred to also as a compound (1)).

$$A\text{-}O\text{—}[R^{f1}O\text{—}R^{f2}O]_n\text{—}B \tag{1}$$

provided that symbols in the formula (1) are as follows:
 n: an integer of at least 2,
 $R^{f1}$: a perfluorodimethylene group,
 $R^{f2}$: a $C_{3-18}$ perfluoroalkylene group which may have an etheric oxygen atom between carbon atoms,
 A: a $C_{1-6}$ perfluoroalkyl group, a $C_{2-6}$ perfluoroalkyl group having an etheric oxygen atom, or B,
 B: a group represented by the following formula (2):

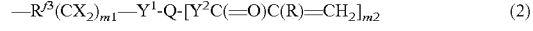

$$-R^{f3}(CX_2)_{m1}-Y^1\text{-}Q\text{-}[Y^2C(=O)C(R)=CH_2]_{m2} \tag{2}$$

provided that symbols in the formula (2) are as follows:
 $R^{f3}$: a $C_{1-20}$ perfluoroalkylene group which may have an etheric oxygen atom between carbon atoms,
 X: a hydrogen atom or a fluorine atom,
 m1: 0 or 1,
 $Y^1$: a single bond, —C(=O)NH— (provided that Q is bonded to N), —OC(=O)NH— (provided that Q is bonded to N), —O—, —C(=O)O— (provided that Q is bonded to O), —OC(=O)O—, —NHC(=O)NH— or —NHC(=O)
O— (provided that Q is bonded to O),
   Q: a single bond or a (m2+1) valent organic group,
   $Y^2$: —O—, —NH— or —NHC(=O)O—$(C_kH_{2k})$—O—
(provided that k is an integer of from 1 to 10, and Q is
bonded to N),
   R: a hydrogen atom or a methyl group,
   m2: an integer of at least 1,
provided that in the formula (2), when m1 is 0, $Y^1$ is not
—O—, —OC(=O)NH— or —OC(=O)—, when $Y^1$ is
—C(=O)NH—, —OC(=O)NH—, —O—, —C(=O)O—,
—OC(=O)O—, —NHC(=O)NH— or —NHC(=O)O—,
Q is a (m2+1) valent organic group, and when each of $Y^1$ and
$Y^2$ is —O—, Q is not a single bond.
   In the formula (1), the poly(oxyperfluoroalkylene) chain
is the portion represented by $[R^{f1}O—R^{f2}O]_n$.
   In the formula (1), n is an integer of at least 2. If the
number average molecular weight of the compound (1) is
too large, the number of (meth)acryloyl groups present per
a unit molecular weight decreases, and the abrasion resistance decreases. Therefore, the upper limit of n is preferably
45, and n is preferably from 4 to 40, particularly preferably
from 5 to 35.
   $R^{f1}$ in the formula (1) is a perfluorodimethylene group (i.e.
$CF_2CF_2$). Since $R^{f1}$ is a perfluorodimethylene group (i.e.
$CF_2CF_2$), the compound (1) has high thermal and chemical
stability and is capable of imparting excellent fingerprint
stain removability to the hard coating layer.
   $R^{f2}$ in the formula (1) is a $C_{3-18}$ perfluoroalkylene group
which may have an etheric oxygen atom between carbon
atoms. $R^{f2}$ may be linear or branched. With a view to
imparting excellent oil-based ink repellency to the hard
coating layer, it is preferably linear. $R^{f2}$ is preferably a $C_{3-6}$
perfluoroalkylene group, or a $C_{6-18}$ perfluoroalkylene group
having an etheric oxygen atom between carbon atoms,
which has a structure wherein two or three $C_{3-6}$ perfluoroalkylene groups are repeated via an etheric oxygen atom.
   With a view to sufficiently imparting oil-based ink repellency to the hard coating layer, $R^{f2}$ is preferably a $C_4$
perfluoroalkylene group, particularly preferably a perfluorotetramethylene group (i.e. $CF_2CF_2CF_2CF_2$).
   As specific examples for the unit $[R^{f1}O—R^{f2}O]$, the
following may be mentioned.
   $(CF_2CF_2O—CF_2CF_2CF_2O)$,
   $(CF_2CF_2O—CF_2CF_2CF_2CF_2O)$,
   $(CF_2CF_2O—CF_2CF_2CF_2CF_2CF_2O)$,
   $(CF_2CF_2O—CF_2CF_2CF_2CF_2CF_2CF_2O)$,
   $(CF_2CF_2O—CF(CF_3)CF_2O)$,
   $(CF_2CF_2O—CF_2CF_2OCF_2CF_2CF_2O)$,
   $(CF_2CF_2O—CF_2CF_2OCF_2CF_2CF_2CF_2O)$,
   $(CF_2CF_2O—CF_2CF_2OCF_2CF_2CF_2CF_2CF_2O)$,
   $(CF_2CF_2O—CF_2CF_2OCF_2CF_2CF_2CF_2CF_2CF_2O)$,
   $(CF_2CF_2O—CF_2CF_2OCF(CF_3)CF_2O)$,
   $(CF_2CF_2O—CF_2CF_2CF_2OCF_2CF_2O)$,
   $(CF_2CF_2O—CF_2CF_2CF_2OCF_2CF_2CF_2O)$,
   $(CF_2CF_2O—CF_2CF_2CF_2OCF_2CF_2CF_2CF_2O)$,
   $(CF_2CF_2O—CF_2CF_2CF_2OCF_2CF_2CF_2CF_2CF_2O)$,
   $(CF_2CF_2O—CF_2CF_2CF_2OCF(CF_3)CF_2O)$,
   $(CF_2CF_2O—CF_2CF_2CF_2CF_2OCF_2CF_2O)$,
   $(CF_2CF_2O—CF_2CF_2CF_2CF_2OCF_2CF_2CF_2O)$,
   $(CF_2CF_2O—CF_2CF_2CF_2CF_2OCF_2CF_2CF_2CF_2O)$,
   $(CF_2CF_2O—CF_2CF_2CF_2CF_2OCF_2CF_2CF_2CF_2CF_2O)$,
   $(CF_2CF_2O—CF_2CF_2CF_2CF_2OCF(CF_3)CF_2O)$,
   $(CF_2CF_2O—CF_2CF_2CF_2CF_2CF_2OCF_2CF_2O)$,
   $(CF_2CF_2O—CF_2CF_2CF_2CF_2CF_2OCF_2CF_2CF_2O)$,
   $(CF_2CF_2O—CF_2CF_2CF_2CF_2CF_2OCF_2CF_2CF_2CF_2O)$,
   $(CF_2CF_2O—CF_2CF_2CF_2CF_2CF_2OCF(CF_3)CF_2O)$,
   $(CF_2CF_2O—CF_2CF_2CF_2CF_2CF_2CF_2OCF_2CF_2O)$,
   $(CF_2CF_2O—CF(CF_3)CF_2O—CF_2CF_2O)$,
   $(CF_2CF_2O—CF(CF_3)CF_2OCF(CF_3)CF_2O)$,
   $(CF_2CF_2O—CF_2CF_2CF_2OCF_2CF_2CF_2O)$,
   $(CF_2CF_2O—CF(CF_3)CF_2OCF_2CF_2CF_2O)$,
   $(CF_2CF_2O—CF_2CF_2OCF_2CF_2OCF_2CF_2O)$,
   $(CF_2CF_2O—CF_2CF_2OCF_2CF_2OCF_2CF_2CF_2O)$,
   $(CF_2CF_2—OCF_2CF_2OCF_2CF_2OCF(CF_3)CF_2O)$,
   $(CF_2CF_2—OCF_2CF_2OCF_2CF_2CF_2OCF_2CF_2O)$,
   $(CF_2CF_2—OCF_2CF_2OCF(CF_3)CF_2OCF_2CF_2O)$,
   $(CF_2CF_2—OCF_2CF_2OCF_2CF_2CF_2OCF_2CF_2CF_2O)$,
   $(CF_2CF_2—OCF_2CF_2OCF_2CF_2CF_2OCF(CF_3)CF_2O)$,
   $(CF_2CF_2O—CF_2CF_2OCF(CF_3)CF_2OCF_2CF_2CF_2O)$,
   $(CF_2CF_2—OCF_2CF_2OCF(CF_3)CF_2OCF(CF_3)CF_2O)$,
   $(CF_2CF_2O—CF_2CF_2OCF_2CF_2CF_2O—CF_2CF_2O)$,
   $(CF_2CF_2—OCF_2CF_2CF_2OCF_2CF_2OCF_2CF_2O)$,
   $(CF_2CF_2—OCF_2CF_2CF_2OCF_2CF_2OCF_2CF_2CF_2O)$,
   $(CF_2CF_2—OCF_2CF_2CF_2OCF_2CF_2OCF(CF_3)CF_2O)$,
   $(CF_2CF_2O—CF(CF_3)CF_2OCF_2CF_2OCF_2CF_2CF_2O)$,
   $(CF_2CF_2O—CF(CF_3)CF_2OCF_2CF_2OCF(CF_3)CF_2O)$,
   $(CF_2CF_2O—CF_2CF_2CF_2OCF_2CF_2OCF_2CF_2O)$,
   $(CF_2CF_2—OCF_2CF_2CF_2OCF(CF_3)CF_2OCF_2CF_2O)$,
   $(CF_2CF_2—OCF(CF_3)CF_2OCF_2CF_2OCF_2CF_2O)$,
   $(CF_2CF_2O—CF(CF_3)CF_2OCF(CF_3)CF_2OCF_2CF_2O)$,
   $(CF_2CF_2O—CF_2CF_2CF_2CF_2OCF_2CF_2OCF_2CF_2O)$, etc.
   As specific examples for a unit in the poly(oxyperfluoroalkylene) chain in the present invention other than
$[R^{f1}O—R^{f2}O]$, the following may be mentioned.
   $(CF_2OCF_2CF_2—OCF_2CF_2CF_2O)$,
   $(CF_2OCF_2CF_2O—CF_2CF_2CF_2CF_2O)$,
   $(CF_2OCF_2CF_2—OCF_2CF_2CF_2CF_2CF_2O)$,
   $(CF_2OCF_2CF_2O—CF_2CF_2CF_2CF_2CF_2CF_2O)$,
   $(CF_2OCF_2CF_2—OCF(CF_3)CF_2O)$,
   $(CF_2OCF_2CF_2OCF_2CF_2O—CF_2CF_2CF_2O)$,
   $(CF_2OCF_2CF_2OCF_2CF_2—OCF_2CF_2CF_2O)$,
   $(CF_2OCF_2CF_2OCF_2CF_2—OCF_2CF_2CF_2CF_2O)$,
   $(CF_2OCF_2CF_2OCF_2CF_2—OCF_2CF_2CF_2CF_2CF_2O)$,
   $(CF_2OCF_2CF_2OCF_2CF_2O—CF(CF_3)CF_2O)$,
   $(CF_2OCF_2CF_2—OCF_2CF_2CF_2—OCF_2CF_2O)$,
   $(CF_2OCF_2CF_2—OCF_2CF_2CF_2OCF_2CF_2O)$,
   $(CF_2OCF_2CF_2—OCF_2CF_2CF_2OCF_2CF_2CF_2O)$,
   $(CF_2OCF_2CF_2—OCF_2CF_2CF_2OCF_2CF_2CF_2CF_2O)$,
   $(CF_2OCF_2CF_2—OCF_2CF_2CF_2OCF(CF_3)CF_2O)$,
   $(CF_2OCF_2CF_2—OCF_2CF_2CF_2CF_2—OCF_2CF_2O)$,
   $(CF_2OCF_2CF_2—OCF_2CF_2CF_2CF_2OCF_2CF_2O)$,
   $(CF_2OCF_2CF_2O—CF_2CF_2CF_2CF_2OCF_2CF_2CF_2O)$,
   $(CF_2OCF_2CF_2—OCF_2CF_2CF_2CF_2OCF(CF_3)CF_2O)$,
   $(CF_2OCF_2CF_2O—CF_2CF_2CF_2CF_2O—CF_2CF_2O)$,
   $(CF_2OCF_2CF_2—OCF_2CF_2CF_2CF_2OCF_2CF_2O)$,
   $(CF_2OCF_2CF_2—OCF_2CF_2CF_2CF_2OCF(CF_3)CF_2O)$,
   $(CF_2OCF_2CF_2—OCF_2CF_2CF_2CF_2CF_2CF_2—OCF_2CF_2O)$,
   $(CF_2OCF_2CF_2O—CF(CF_3)CF_2O—CF_2CF_2O)$,
   $(CF_2OCF_2CF_2O—CF(CF_3)CF_2OCF(CF_3)CF_2O)$,
   $(CF_2OCF_2CF_2O—CF(CF_3)OCF_2CF_2CF_2O)$,
   $(CF_2OCF_2CF_2—OCF(CF_3)CF_2OCF_2CF_2CF_2CF_2O)$,
   $(CF_2OCF_2CF_2OCF_2CF_2OCF_2CF_2—OCF_2CF_2CF_2O)$,
   $(CF_2OCF_2CF_2OCF_2CF_2OCF_2CF_2—OCF_2CF_2CF_2CF_2O)$,
   $(CF_2OCF_2CF_2OCF_2CF_2OCF_2CF_2—OCF(CF_3)CF_2O)$,
   $(CF_2OCF_2CF_2OCF_2CF_2—OCF_2CF_2—OCF_2CF_2O)$,
   $(CF_2OCF_2CF_2OCF_2CF_2—OCF(CF_3)CF_2—OCF_2CF_2O)$,
   $(CF_2OCF_2CF_2OCF_2CF_2—OCF_2CF_2CF_2OCF_2CF_2CF_2O)$,
   $(CF_2OCF_2CF_2OCF_2CF_2—OCF_2CF_2CF_2OCF(CF_3)CF_2O)$,
   $(CF_2OCF_2CF_2OCF(CF_3)CF_2OCF_2CF_2CF_2O)$,
   $(CF_2OCF_2CF_2—OCF(CF_3)CF_2OCF_2CF_2CF_2OCF_2CF_2CF_2O)$, ($CF_2OCF_2CF_2OCF_2CF_2$—$OCF(CF_3)CF_2OCF(CF_3)CF_2O$),
($CF_2OCF_2CF_2OCF_2CF_2$—$OCF_2CF_2CF_2CF_2$—$OCF_2CF_2O$),
($CF_2OCF_2CF_2O$—$CF_2CF_2CF_2O$—$CF_2CF_2OCF_2CF_2O$),
($CF_2OCF_2CF_2$—$OCF_2CF_2CF_2$—$OCF_2CF_2$—$OCF_2CF_2CF_2O$),
($CF_2OCF_2CF_2$—$OCF_2CF_2CF_2$—$OCF_2CF_2$—$OCF(CF_3)CF_2O$),
($CF_2OCF_2CF_2O$—$CF(CF_3)CF_2O$—$CF_2CF_2O$—$CF_2CF_2CF_2O$),
($CF_2OCF_2CF_2$—$OCF(CF_3)CF_2$—$OCF_2CF_2$—$OCF(CF_3)CF_2O$),
($CF_2OCF_2CF_2$—$OCF_2CF_2OCF_2CF_2CF_2$—$OCF_2CF_2O$),
($CF_2OCF_2CF_2$—$OCF_2CF_2CF_2OCF(CF_3)CF_2$—$OCF_2CF_2O$),
($CF_2OCF_2CF_2O$—$CF(CF_3)CF_2OCF_2CF_2CF_2O$—$CF_2CF_2O$),
($CF_2OCF_2CF_2$—$OCF(CF_3)CF_2OCF(CF_3)CF_2$—$OCF_2CF_2O$),
($CF_2OCF_2CF_2$—$OCF_2CF_2CF_2CF_2$—$OCF_2CF_2OCF_2CF_2O$), etc.

As the unit [$R^{f1}O$—$R^{f2}O$], the following are preferred with a view to imparting excellent antifouling properties (oil-based ink repellency, fingerprint stain removability) to the hard coating layer.
($CF_2CF_2O$—$CF_2CF_2CF_2O$),
($CF_2CF_2O$—$CF_2CF_2CF_2CF_2O$),
($CF_2CF_2O$—$CF_2CF_2CF_2OCF_2CF_2CF_2O$),
($CF_2CF_2O$—$CF_2CF(CF_3)OCF_2CF_2CF_2O$),
($CF_2CF_2O$—$CF_2CF_2CF_2CF_2OCF(CF_3)CF_2O$).

<Group A>

The terminal group A is a $C_{1-6}$ perfluoroalkyl group, a $C_{2-6}$ perfluoroalkyl group having an etheric oxygen atom, or B. With a view to imparting excellent antifouling properties (oil-based ink repellency, fingerprint stain removability) to the hard coating layer, it is preferably a $C_{1-6}$ perfluoroalkyl group, or a $C_{2-6}$ perfluoroalkyl group having an etheric oxygen atom, particularly preferably a $C_{1-6}$ perfluoroalkyl group. The perfluoroalkyl group may be linear or branched.

The following may be mentioned as specific examples of A.

As a $C_{1-6}$ perfluoroalkyl group: $CF_3$—, $CF_3CF_2$—, $CF_3(CF_2)_2$—, $CF_3(CF_2)_3$—, $CF_3(CF_2)_4$—, $CF_3(CF_2)_5$—, $CF_3CF(CF_3)$—, etc.

As a $C_{2-6}$ perfluoroalkyl group having an etheric oxygen atom: $CF_3OCF_2CF_2$—, $CF_3O(CF_2)_3$—, $CF_3O(CF_2)_4$—, $CF_3O(CF_2)_5$—, $CF_3OCF_2CF_2OCF_2CF_2$—, $CF_3CF_2OCF_2CF_2$—, $CF_3CF_2O(CF_2)_3$—, $CF_3CF_2O(CF_2)_4$—, $CF_3CF_2OCF_2CF_2OCF_2CF_2$—, $CF_3(CF_2)_2OCF_2CF_2$—, $CF_3(CF_2)_2O(CF_2)_3$—, $CF_3(CF_2)_2OCF(CF_3)CF_2$—, $CF_3CF(CF_3)OCF_2CF_2$—, $CF_3CF(CF_3)O(CF_2)_3$—, $CF_3CF(CF_3)OCF(CF_3)CF_2$—, $CF_3(CF_2)_3OCF_2CF_2$—, etc.

A is preferably $CF_3$— or $CF_3CF_2$— with a view to imparting excellent antifouling properties (oil-based ink repellency, fingerprint stain removability) to the hard coating layer.

<Group B>

In the compound (1), when two B are present in one molecule, they may be the same or different.

As B, preferred is such that the combination of $Y^1$, Q, $Y^2$ and m1 in the formula (2) is one of the following 1 to 5.

1. $Y^1$: single bond, Q: single bond, $Y^2$: —O—, m1=1
2. $Y^1$: —C(=O)NH—, Q: (m2+1) valent organic group, $Y^2$: —O— or —NH—, m1=0
3. $Y^1$: —OC(=O)NH—, Q: (m2+1) valent organic group, $Y^2$: —O— or —NH—, m1=1
4. $Y^1$: —O—, Q: (m2+1) valent organic group, $Y^2$: —O—, m1=1
5. $Y^1$: —OC(=O)NH—, Q: (m2+1) valent organic group, $Y^2$: —NHC(=O)O—($C_kH_{2k}$)—O—, m1=1

As B, particularly preferred are groups represented by the formulae (2-1) to (2-6), since the production of the compound (1) is thereby easy.

$$—R^{f3}CX_2—OC(=O)C(R)=CH_2 \tag{2-1}$$

$$—R^{f3}—C(=O)NH-Q^2-OC(=O)C(R)=CH_2 \tag{2-2}$$

$$—R^{f3}—C(=O)NH-Q^2-NHC(=O)C(R)=CH_2 \tag{2-3}$$

$$—R^{f3}CX_2—OC(=O)NH-Q^2-OC(=O)C(R)=CH_2 \tag{2-4}$$

$$—R^{f3}CX_2—O-Q^2-OC(=O)C(R)=CH_2 \tag{2-5}$$

$$—R^{f3}CX_2—OC(=O)NH-Q-[NHC(=O)O—(C_kH_{2k})—OC(=O)C(R)=CH_2]_{m2} \tag{2-6}$$

Here, $Q^2$ is a bivalent organic group, and $Q^3$ is a trivalent organic group. The two X in $CX_2$ may be the same or different. Further, Q in the formula (2-6) is $Q^2$ or $Q^3$, provided that when Q is $Q^2$, m2 is 1, and when Q is $Q^3$, m2 is 2.

Further, $CX_2$ is preferably $CH_2$ or CFH, particularly preferably $CH_2$. ($C_kH_{2k}$) is a linear or branched alkylene group, preferably ($CH_2$)$_k$, where k is preferably from 2 to 6, more preferably from 2 to 3, particularly preferably 2. In a case where Q in the formula (2-6) is $Q^2$, $Q^2$ is a bivalent group obtained by removing two isocyanate groups from a diisocyate compound represented by $Q^2$(-NCO)$_2$. In a case where Q in the formula (2-6) is $Q^3$, $Q^3$ is a trivalent group obtained by removing three isocyanate groups from a triisocyate compound represented by $Q^3$(-NCO)$_3$.

Hereinafter, a compound (1) wherein B is a group represented by the formula (2-1) is referred to as a compound (1-1), a compound (1) wherein B is a group represented by the formula (2-2) is referred to as a compound (1-2), a compound (1) wherein B is a group represented by the formula (2-3) is referred to as a compound (1-3), a compound (1) wherein B is a group represented by the formula (2-4) is referred to as a compound (1-4), a compound (1) wherein B is a group represented by the formula (2-5) is referred to as a compound (1-5), and a compound (1) wherein B is a group represented by the formula (2-6) is referred to as a compound (1-6) or a compound (1-7).

$$A-O—[R^{f1}O—R^{f2}O]_n—R^{f3}CX_2—OC(=O)C(R)=CH_2 \tag{1-1}$$

$$A-O—[R^{f1}O—R^{f2}O]_n—R^{f3}—C(=O)NH-Q^2-OC(=O)C(R)=CH_2 \tag{1-2}$$

$$A-O—[R^{f1}O—R^{f2}O]_n—R^{f3}—C(=O)NH-Q^2-NHC(=O)C(R)=CH_2 \tag{1-3}$$

$$A-O—[R^{f1}O—R^{f2}O]_n—R^{f3}CX_2—OC(=O)NH-Q^2-PC(=O)C(R)=CH_2 \tag{1-4}$$

$$A-O—[R^{f1}O—R^{f2}O]_n—R^{f3}CX_2—O-Q^2-OC(=O)C(R)=CH_2 \tag{1-5}$$

$$A-O—[R^{f1}O—R^{f2}O]_n—R^{f3}CX_2—OC(=O)NH-Q^3-[NHC(=O)O—(C_kH_{2k})—OC(=O)C(R)=CH_2]_2 \tag{1-6}$$

$$A-O—[R^{f1}O—R^{f2}O]_n—R^{f3}CX_2—OC(=O)NH-Q^2-NHC(=O)O—(C_kH_{2k})—OC(=O)C(R)=CH_2 \tag{1-7}$$

$R^{f3}$ is a $C_{1-20}$ perfluoroalkylene group which may have an etheric oxygen atom. The perfluoroalkylene group may be linear or branched. As shown in the after-described preferred method for producing a compound (1), $R^{f3}$ is preferably a derivative of $[(R^{f1}O)(R^{f2}O)]$. That is, it is preferably a group having terminal $CF_2O$ at the $(R^{f2}O)$ side of $[R^{f1}O—R^{f2}O]$ converted to $CX_2$. For example, in a case where $[R^{f1}O—R^{f2}O]$ is $[CF_2CF_2OCF_2CF_2CF_2CF_2O]$, $—R^{f3}CX_2$ is preferably $—CF_2CF_2OCF_2CF_2CF_2CX_2—$, i.e. $R^{f3}$ is preferably $CF_2CF_2OCF_2CF_2CF_2$.

With a view to imparting excellent antifouling properties (oil-based ink repellency, fingerprint stain removability) to the hard coating layer, the following are preferred.
$—CF_2CF_2OCF_2CF_2—$, $—CF_2CF_2OCF_2CF_2CF_2—$, $—CF_2CF_2OCF_2CF_2CF_2OCF_2CF_2—$, $—CF_2CF_2OCF_2CF(CF_3)OCF_2CF_2—$, and $—CF_2CF_2OCF_2CF_2CF_2CF_2OCF(CF_3)—$.

Q is a single bond or a (m2+1) valent organic group. The (m2+1) valent organic group may, for example, be $Q^2$ or $Q^3$.

$Q^2$ may, for example, be an alkylene group, a poly (oxyalkylene) group, a cycloalkylene group, an arylene group, or a group having any of hydrogen atoms in an alkylene group substituted by a hydroxy group. $Q^2$ is preferably a $C_{2-6}$ alkylene group or a group having any of hydrogen atoms in such an alkylene group substituted by a hydroxy group, since an industrial production is thereby easy.

$Q^3$ may, for example, be an isocyanurate ring, biuret, adduct or the like, derived from a trimer of a diisocyanate.

m2 is an integer of at least 1, and it is preferably 1 or 2, since an industrial production is thereby easy.

In a case where m2 is 2 or more, plural $Q^2$ and R present in one molecule may, respectively, be the same or different from one another. From the viewpoint of availability of raw material and production efficiency, they are, respectively, preferably the same.

Preferred Embodiments

As the compound (1), preferred is a compound having the above-mentioned preferred A and the above-mentioned preferred unit $[R^{f1}O—R^{f2}O]$ combined, and particularly preferred are compounds represented by the following formulae. The compounds represented by the following formulae can easily be produced on an industrial scale and can easily be handled, and they are capable of imparting excellent antifouling properties (oil-based ink repellency, fingerprint stain removability) to the hard coating layer.

$A^1$-O—($CF_2CF_2$O—$CF_2CF_2CF_2CF_2$O)$_n$—
$CF_2CF_2OCF_2CF_2CF_2CH_2$—OC(=O)C(R)=
$CH_2$             (1-1a)

$A^1$-O—($CF_2CF_2$O—$CF_2CF_2CF_2CF_2$O)$_n$—
$CF_2CF_2OCF_2CF_2CF_2$—C(=O)NH-$Q^2$-OC(=O)
C(R)=$CH_2$             (1-2a)

$A^1$-O—($CF_2CF_2$O—$CF_2CF_2CF_2CF_2$O)$_n$—
$CF_2CF_2OCF_2CF_2CF_2$—C(=O)NH-$Q^2$-NHC
(=O)C(R)=$CH_2$             (1-3a)

$A^1$-O—($CF_2CF_2$O—$CF_2CF_2CF_2CF_2$O)$_n$-
$CF_2CF_2OCF_2CF_2CF_2CH_2$—OC(=O)NH-$Q^2$-
OC(=O)C(R)=$CH_2$             (1-4a)

$A^1$-O—($CF_2CF_2$O-$CF_2CF_2CF_2CF_2$O)$_n$—
$CF_2CF_2OCF_2CF_2CF_2CH_2$—O-$Q^2$-OC(=O)
(R)=$CH_2$             (1-5a)

$A^1$-O—($CF_2CF_2$O—$CF_2CF_2CF_2CF_2$O)$_n$—
$CF_2CF_2OCF_2CF_2CF_2CH_2$—OC(=O)NH-$Q^3$-
[NHC(=O)O—($CH_2$)$_2$—OC(=O)C(R)=$CH_2$]$_2$             (1-6a)

$A^1$-O—($CF_2CF_2$O—$CF_2CF_2CF_2CF_2$O)$_n$—
$CF_2CF_2OCF_2CF_2CF_2CH_2$—OC(=O)NH-$Q^2$-
NHC(=O)O—($CH_2$)$_2$—OC(=O)C(R)=$CH_2$             (1-7a)

Here, $A^1$ is $CF_3$— or $CF_3CF_2$—.

Among the above compounds, more preferred are the following compounds.

$A^1$-O—($CF_2CF_2$O—$CF_2CF_2CF_2CF_2$O)$_n$—
$CF_2CF_2OCF_2CF_2CF_2CH_2$—OC(=O)C(R)=
$CH_2$             (1-1a)

$A^1$-O—($CF_2CF_2$O—$CF_2CF_2CF_2CF_2$O)$_n$—
$CF_2CF_2OCF_2CF_2CF_2CH_2$—OC(=O)NH-$Q^2$-
OC(=O)C(R)=$CH_2$             (1-4a)

$A^1$-O—($CF_2CF_2$O—$CF_2CF_2CF_2CF_2$O)$_n$—
$CF_2CF_2OCF_2CF_2CF_2CH_2$—OC(=O)NH-$Q^3$-
[NHC(=O)O—($CH_2$)$_2$—OC(=O)C(R)=$CH_2$]$_2$             (1-6a)

$A^1$-O—($CF_2CF_2$O—$CF_2CF_2CF_2CF_2$O)$_n$—
$CF_2CF_2OCF_2CF_2CF_2CH_2$—OC(=O)NH-$Q^2$-
NHC(=O)O—($CH_2$)$_2$—OC(=O)C(R)=$CH_2$             (1-7a)

(Compound (111))

As the present compound, as a compound in the second embodiment, preferred is a compound represented by the following formula (111) (hereinafter referred to also as a compound (111)).

$$A-O—[(R^{f11}O)_{x1}(R^{f12}O)_{x2}]—B \quad (111)$$

Symbols in the formula (111) are as follows.

x1 and x2: each independently an integer of at least 1.
$R^{f11}$: a $C_4$ perfluoroalkylene group.
$R^{f12}$: a perfluoroalkylene group other than $C_4$.
A: a $C_{1-6}$ perfluoroalkyl group or B.
B: a group represented by the following formula (2).

$$—R^{f3}(CX_2)_{m1}—Y^1-Q-[Y^2C(=O)C(R)=CH_2]_{m2} \quad (2)$$

Symbols in the formula (2) are as defined above.

$R^{f11}$ in the formula (111) is a $C_4$ perfluoroalkylene group. $R^{f11}$ may be linear or branched. With a view to imparting excellent oil-based ink repellency to the hard coating layer, it is preferably linear i.e. $CF_2CF_2CF_2CF_2$.

x2 in the formula (111) is an integer of at least 1. With a view to imparting excellent fingerprint stain removability to the hard coating layer, it is preferably an integer of at least 3, particularly preferably an integer of at least 5. It is preferably an integer of at most 20, particularly preferably at most 10, from such a viewpoint that the compound (111) is thereby excellent in compatibility with other components in the composition for forming a hard coating layer.

$R^{f12}$ in the formula (111) is a perfluoroalkylene group other than $C_4$. $R^{f12}$ may be linear or branched, when it has two or more carbon atoms. It is preferably linear with a view to imparting excellent oil-based ink repellency to the hard coating layer.

$R^{f12}$ is preferably a $C_{1-3}$ perfluoroalkylene group or a $C_{5-15}$ perfluoroalkylene group, particularly preferably a $C_{1-3}$ perfluoroalkylene group or a $C_{5-6}$ perfluoroalkylene group, from such a viewpoint that the compound (111) is thereby excellent in compatibility with other components in the composition for forming a hard coating layer. With a view to imparting excellent fingerprint stain removability to the hard coating layer, a $C_{1-2}$ perfluoroalkylene group is preferred. From the viewpoint of thermal and chemical stability, at least one type of a perfluoroalkylene group other than $C_1$, is preferred. $R^{f12}$ may be one type alone, or two or more types. In the case of two or more types, the number of carbon atoms may be the same or different.

In the formula (111), the bonding order of $(R^{f11}O)$ and $(R^{f12}O)$ in the portion represented by $[(R^{f11}O)_{x1}(R^{f12}O)_{x2}]$ is not particularly limited. They may be arranged in a random, block or alternate form. With a view to imparting excellent antifouling properties (oil-based ink repellency, fingerprint stain removability) to the hard coating layer, they are preferably alternately arranged, and further, it is particularly preferred that the side close to A is $(R^{f12}O)$, and the side close to B is $(R^{f11}O)$.

$[(R^{f11}O)_{x1}(R^{f12}O)_{x2}]$ is particularly preferably the following poly(oxyperfluoroalkylene) chains, with a view to imparting excellent antifouling properties (oil-based ink repellency, fingerprint stain removability) to the hard coating layer.

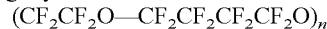

Here, n is the number of repeating units constituted by the above two types of oxyperfluoroalkylene groups, and is an integer of at least 1.

<Group A, Group B>

Types and preferred ranges are the same as described above.

Preferred Embodiments

As the compound (111), preferred are the above mentioned compounds (1-1a) to (1-7a), and more preferred are the compounds (1-1a), (1-4a), (1-6a) and (1-7a).

[Method for Producing Fluorinated Ether Compound]

The compound (1-1) can be produced by a method of reacting a compound (5) represented by the following formula (5) and $ClC(=O)C(R)=CH_2$ in the presence of a base (such as triethylamine).

$$A\text{-}O\text{---}[R^{f1}O\text{---}R^{f2}O]_n\text{---}R^{f3}CX_2\text{---}OH \quad (5)$$

The compound (1-2) can be produced by a method of reacting a compound (4) represented by the following formula (4) and $ClC(=O)C(R)=CH_2$ in the presence of a base (such as triethylamine).

$$A\text{-}O\text{---}[R^{f1}O\text{---}R^{f2}O]_n\text{---}R^{f3}\text{---}C(=O)NH\text{-}Q^2\text{-}OH \quad (4)$$

The compound (1-3) can be produced by a method of reacting a compound (3) represented by the following formula (3) and $ClC(=O)C(R)=CH_2$ in the presence of a base (such as triethylamine).

$$A\text{-}O\text{---}[R^{f1}O\text{---}R^{f2}O]_n\text{---}R^{f3}\text{---}C(=O)NH\text{-}Q^2\text{-}NH_2 \quad (3)$$

The compound (1-4) can be produced by a method of reacting the compound (5) and $OCN\text{-}Q^2\text{-}OC(=O)C(R)=CH_2$ in the presence of a urethanization catalyst.

The compound (1-5) can be produced by a method of reacting the compound (5) and $Ep\text{-}R^3\text{---}OC(=O)C(R)=CH_2$. Ep is an epoxy group, and $R^3$ is an alkylene group. After the reaction, $Ep\text{-}R^3$-becomes $\text{---}CH_2CH(OH)\text{---}R^3\text{---}$ i.e. $Q^2$.

The compound (1-6) can be produced by a method of reacting the compound (5), $HO\text{---}(CH_2)_2\text{---}OC(=O)C(R)=CH_2$ and a triisocyanate compound (such as a trimer of a diisocyanate compound) in the presence of a urethanization catalyst.

The compound (1-7) can be produced by a method of reacting the compound (5), $HO\text{---}(CH_2)_2\text{---}OC(=O)C(R)=CH_2$ and a diisocyanate compound in the presence of a urethanization catalyst.

The compound (5), (4) or (3) can be produced by a known method depending upon the structure of $A\text{-}O\text{---}[R^{f1}O\text{---}R^{f2}O]_n\text{---}$. The method for producing the compound (5), (4) or (3) is, for example, as follows.

(Method for Producing Compound (5))

The method for producing the compound (5) will be described with reference to the case of a compound (5a) represented by the following formula (5a).

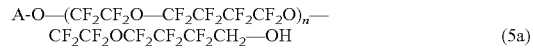

<Method for Producing Compound (5a)>

A compound (12a) represented by the following formula (12a) is subjected to hydrogen reduction by means of a reducing agent (such as sodium borohydride or aluminum lithium hydride) to obtain a compound (11a) represented by the following formula (11a).

$$CF_2=CFO\text{---}CF_2CF_2CF_2C(=O)OCH_3 \quad (12a)$$

$$CF_2=CFO\text{---}CF_2CF_2CF_2CH_2OH \quad (11a)$$

The compound (11a) and an alkanol or polyfluoroalkanol (such as methanol, ethanol, 1-propanol, 2-propanol, 2,2,2-trifluoroethanol, 2,2,3,3-tetrafluoropropanol or 1,1,1,3,3,3-hexafluoro-2-propanol, hereinafter referred to as $A^2\text{-}OH$) are reacted in the presence of a base or quaternary ammonium salt (such as potassium carbonate, sodium carbonate, potassium fluoride, cesium fluoride, sodium hydride, tert-butoxy potassium, sodium hydroxide, potassium hydroxide, tetrabutylammonium chloride or tetrabutylammonium bromide), to obtain a compound (10a) represented by the following formula (10a).

$$A^2\text{-}O\text{---}(CF_2CFHO\text{---}CF_2CF_2CF_2CH_2O)_{n+1}\text{---}H \quad (10a)$$

By controlling the amount of $A^2\text{-}OH$ to be used against the compound (11a), it is possible to synthesize a compound (10a) having a desired number average molecular weight. Or, $A^2\text{-}OH$ may be the compound (11a) itself, and a compound (10a) having a desired number average molecular weight may be synthesized by controlling the reaction time or separation and purification of the product.

The synthesis of the compound (11a) and the synthesis of the compound (10a) by its polyaddition reaction may be carried out in accordance with the known methods disclosed in U.S. Pat. No. 5,134,211.

By an esterification reaction of the compound (10a) and $ClC(=O)R^4$, a compound (9a) represented by the following formula (9a) is obtainable. Here, $R^4$ is a alkyl group, polyfluoroalkyl group or perfluoroalkyl group, or a $C_{2-11}$ alkyl group, polyfluoroalkyl group or perfluoroalkyl group, having an etheric oxygen atom.

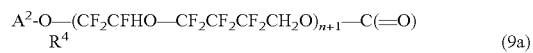

Further, by substituting fluorine atoms for hydrogen atoms in the compound (9a) by fluorine gas, a compound (7a) represented by the following formula (7a) is obtainable. Here, $R^{f4}$ is a $C_{1-11}$ perfluoroalkyl group, or a $C_{2-11}$ perfluoroalkyl group having an etheric oxygen atom. A is a group having hydrogen atoms contained in $A^2$ substituted by fluorine atoms. Such a fluorination step may, for example, be carried out in accordance with e.g. the method disclosed in WO2000/56694.

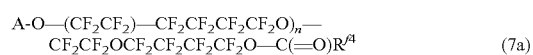

By reacting the compound (7a) with an alcohol (such as methanol, ethanol, 1-propanol or 2-propanol, hereinafter referred to as $R^2OH$, where $R^2$ is an alkyl group), a compound (6a) represented by the following formula (6a) is obtainable.

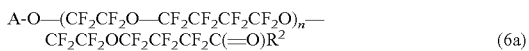
$$A\text{-}O\text{---}(CF_2CF_2O\text{---}CF_2CF_2CF_2CF_2O)_n\text{---}$$
$$CF_2CF_2OCF_2CF_2CF_2C(\!=\!O)R^2 \quad (6a)$$

By subjecting the compound (6a) to hydrogen reduction by means of a reducing agent (such as sodium boron hydride or aluminum lithium hydride), the compound (5) is obtainable.

(Method for Producing Compound (4))

The method for producing the compound (4) will be described with reference to the case of a compound (4a) represented by the following formula (4a).

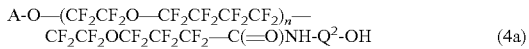
$$A\text{-}O\text{---}(CF_2CF_2O\text{---}CF_2CF_2CF_2CF_2)_n\text{---}$$
$$CF_2CF_2OCF_2CF_2CF_2\text{---}C(\!=\!O)NH\text{-}Q^2\text{-}OH \quad (4a)$$

<Method for Producing Compound (4a)>

By reacting the compound (7a) with $H_2N\text{-}Q^2\text{-}OH$, a compound (4a) is obtainable.

(Method for Producing Compound (3))

The method for producing the compound (3) will be described with reference to the case of a compound (3a) represented by the following formula (3a).

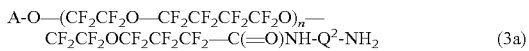
$$A\text{-}O\text{---}(CF_2CF_2O\text{---}CF_2CF_2CF_2CF_2O)_n\text{---}$$
$$CF_2CF_2OCF_2CF_2CF_2\text{---}C(\!=\!O)NH\text{-}Q^2\text{-}NH_2 \quad (3a)$$

<Method for Producing Compound (3a)>

By reacting a compound (8a) represented by the following formula (8a) obtained by changing the terminal $OR^2$ of the above compound (6a) to a chlorine atom by a common method, with $H_2N\text{-}Q^2\text{-}NH_2$, a compound (3a) is obtainable.

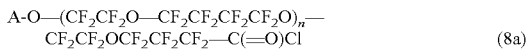
$$A\text{-}O\text{---}(CF_2CF_2O\text{---}CF_2CF_2CF_2CF_2O)_n\text{---}$$
$$CF_2CF_2OCF_2CF_2CF_2\text{---}C(\!=\!O)Cl \quad (8a)$$

[Composition for Forming Hard Coating Layer]

The composition for forming a hard coating layer of the present invention (hereinafter referred to also as the present composition) comprises the present compound, a photopolymerizable compound (provided that the present compound is excluded) and a photopolymerization initiator. The composition for forming a hard coating layer of the present invention may further contain a medium and other additives, as the case requires.

(Photopolymerizable Compound)

The photopolymerizable compound is a monomer which initiates a polymerization reaction when irradiated with active energy rays in the presence of the after-described photopolymerization initiator.

The photopolymerizable compound may be a polyfunctional polymerizable monomer (a1) (hereinafter referred to also as a monomer (a1)) or a monofunctional polymerizable monomer (a2) (hereinafter referred to also as a monomer (a2).), provided that the present compound is excluded.

As the photopolymerizable compound, one type may be used alone, or two or more types may be used in combination. As the photopolymerizable compound, one containing the monomer (a1) as an essential component, is preferred with a view to imparting excellent abrasion resistance to the hard coating layer.

The monomer (a1) may be a compound having at least 2 (meth)acryloyl groups in one molecule. The number of (meth)acryloyl groups is preferably at least 3, particularly preferably from 3 to 30, in one molecule.

The monomer (a1) is preferably a monomer (a11) which has at least 3 (meth)acryloyl groups in one molecule and which has a molecular weight of at most 120 per one (meth)acryloyl group, with a view to imparting excellent abrasion resistance to the hard coating layer.

The monomer (a11) may be a compound which is a reaction product of trimethylolpropane, pentaerythritol or polypentaerythritol with acrylic acid or methacrylic acid and which has at least 3, more preferably from 4 to 20, (meth) acryloyl groups. As specific examples, trimethylolpropane tri(meth)acrylate, pentaerythritol tri(meth)acrylate, pentaerythritol tetra(meth)acrylate, dipentaerythritol hexa(meth)acrylate, etc. may be mentioned.

Also preferred as the monomer (a1) is a monomer (a12) which has a urethane bond in its molecule and which has at least 3 (meth)acryloyl groups in one molecule, from such a viewpoint that the urethane bond functions as a pseudo-crosslinking point by the action of hydrogen bonding and with a view to imparting excellent abrasion resistance to the hard coating layer even if the molecular weight per one (meth)acryloyl group is not small.

The monomer (a12) may, for example, be tris(acryloyloxyethyl) isocyanurate or the following compounds.

A compound which is a reaction product of pentaerythritol or polypentaerythritol, a polyisocyanurate and a hydroxyalkyl (meth)acrylate and which has at least 3, more preferably from 4 to 20, (meth)acryloyl groups.

A compound which is a reaction product of pentaerythritol poly(meth)acrylate having a hydroxy group or polypentaerythritol poly(meth)acrylate having a hydroxy group, and a polyisocyanate and which has at least 3, more preferably from 4 to 20, (meth)acryloyl groups.

The monomer (a2) may be a compound having one (meth)acryloyl group in one molecule. As specific examples, the following compounds may be mentioned.

An alkyl (meth)acrylate wherein the alkyl group has from 1 to 13 carbon atoms, allyl (meth)acrylate, benzyl (meth) acrylate, butoxyethyl (meth)acrylate, butanediol (meth) acrylate, butoxytriethylene glycol mono(meth)acrylate, tert-butylaminoethyl (meth)acrylate, 3-chloro-2-hydroxypropyl (meth)acrylate, 2-cyanoethyl (meth)acrylate, cyclohexyl (meth)acrylate, 2,3-dibromopropyl (meth)acrylate, dicyclopentenyl (meth)acrylate, N,N-diethylaminoethyl (meth) acrylate, N,N-dimethylaminoethyl (meth)acrylate, 2-ethoxyethyl (meth)acrylate, 2-(2-ethoxyethoxyl)ethyl (meth)acrylate, 2-ethylhexyl (meth)acrylate, glycerol (meth) acrylate, glycidyl (meth)acrylate, heptadecafluorodecyl (meth)acrylate, 2-hydroxyethyl (meth)acrylate, 2-hydroxy-3-(meth)acryloyloxypropyltrimethyl ammonium chloride, 2-hydroxypropyl (meth)acrylate, γ-(meth)acryloxypropyltrimethoxy silane, 2-methoxyethyl (meth)acrylate, methoxydiethylene glycol (meth)acrylate, methoxytriethylene glycol (meth)acrylate, methoxytetraethylene glycol (meth)acrylate, methoxydipropylene glycol (meth)acrylate, methoxylated cyclodecatriene (meth)acrylate, morpholine (meth)acrylate, nonylphenoxypolyethylene glycol (meth)acrylate, nonylphenoxypolypropylene glycol (meth)acrylate, octafluoropentyl (meth)acrylate, phenoxyhydroxypropyl (meth)acrylate, phenoxyethyl (meth)acrylate, phenoxydiethylene glycol (meth)acrylate, phenoxytetraethylene glycol (meth) acrylate, phenoxyhexaethylene glycol (meth)acrylate, phenoxy (meth)acrylate, polypropylene glycol (meth)acrylate, 2-sodium sulfonate ethoxy (meth)acrylate, tetrafluoropropyl (meth)acrylate, tetrahydrofurfuryl (meth)acrylate, trifluoroethyl (meth)acrylate, vinyl acetate, N-vinyl caprolactam, N-vinyl pyrrolidone, dicyclopentadienyl (meth)acrylate, isobornyl acrylate, etc.

(Photopolymerization Initiator)

As the photopolymerization initiator, a known photopolymerization initiator may be used. For example, an aryl ketone type photopolymerization initiator (such as an acetophenone, a benzophenone, an alkylaminobenzophenone, a benzyl, a benzoin, a benzoin ether, a benzyl dimethyl ketal, a benzoin benzoate or an α-acyloxime ester), a sulfur-containing photopolymerization initiator (such as a sulfide or a thioxanthone), an acyl phosphine oxide (such as an acyl diaryl phosphine oxide) or other photopolymerization initiators may be mentioned. As the photopolymerization initiator, one type may be used alone, or two or more types may be used in combination. The photopolymerization initiator may be used in combination with a photosensitizer such as an amine.

The following compounds may be mentioned as specific examples of the photopolymerization initiator.

4-phenoxydichloroacetophenone, 4-tert-butyl-dichloroacetophenone, 4-tert-butyl-trichloroacetophenone, diethoxyacetophenone, 2-hydroxy-2-methyl-1-phenylpropan-1-one, 1-(4-isopropylphenyl)-2-hydroxy-2-methylpropan-1-one, 1-(4-dodecylphenyl)-2-methylpropan-1-one, 1-{4-(2-hydroxyethoxy)phenyl}-2-hydroxy-2-methyl-propan-1-one, 1-hydroxycyclohexylphenyl ketone, 2-methyl-1-{4-(methylthio)phenyl}-2-morpholinopropan-1-one.

Benzyl, benzoin, benzoin methyl ether, benzoin ethyl ether, benzoin isopropyl ether, benzoin isobutyl ether, benzyl dimethyl ketal, benzophenone, benzoyl benzoate, benzoyl methyl benzoate, 4-phenylbenzophenone, hydroxybenzophenone, acrylated benzophenone, 3,3'-dimethyl-4-methoxybenzophenone, 3,3',4,4'-tetrakis(t-butylperoxycarbonyl)benzophenone, 9,10-phenanthrenequinone, camphorquinone, dibenzosuberone, 2-ethyl anthraquinone, 4',4'-diethylisophthalophenone, (1-phenyl-1,2-propandione-2(o-ethoxycarbonyl)oxime), α-acyloxime ester, methylphenyl glyoxylate.

4-benzoyl-4'-methyldiphenyl sulfide, thioxanthone, 2-chlorothioxanthone, 2-methylthioxanthone, 2,4-dimethylthioxanthone, isopropylthioxanthone, 2,4-dichlorothioxanthone, 2,4-diethylthioxanthone, 2,4-dipropylthioxanthone, 2,4,6-trimethylbenzoyldiphenylphosphine oxide, benzoyldiphenylphosphine oxide, 2,6-dimethylbenzoyldiphenylphosphine oxide, bis(2,6-dimethoxybenzoyl)-2,4,4-trimethylpentylphosphine oxide, etc.

(Medium)

The present composition may further contain a medium as the case requires. By containing the medium, the present composition may be adjusted with respect to its formulation, viscosity, surface tension, etc., and may be controlled to have liquid physical properties suitable for a coating method. The coating film of the composition for forming a hard coating layer containing the medium is hardened after removing the medium, to form a hard coating layer.

The medium is preferably an organic solvent. The organic solvent is preferably an organic solvent having a boiling point suitable for the method for applying the present composition.

The organic solvent may be a fluorinated organic solvent or a non-fluorinated organic solvent, or may contain both of them.

The fluorinated organic solvent may, for example, be a fluoro-alkane, a fluoro-aromatic compound, a fluoro-alkyl ether, a fluoro-alkylamine or a fluoro-alcohol.

The fluoro-alkane is preferably a $C_{4-6}$ compound. Commercial products may, for example, be $C_6F_{13}H$ (AC-2000, trade name, manufactured by Asahi Glass Co., Ltd.), $C_6F_{13}C_2H_5$ (AC-6000, trade name, manufactured by Asahi Glass Co., Ltd.), $C_2F_5CHFCHFCF_3$ (Vertrel, trade name, manufactured by DuPont), etc.

The fluoro-aromatic compound may, for example, be hexafluorobenzene, trifluoromethylbenzene, perfluorotoluene or bis(trifluoromethyl)benzene.

The fluoro-alkyl ether is preferably a $C_{4-12}$ compound. Commercial products may, for example, be $CF_3CH_2OCF_2CF_2H$ (AE-3000, trade name, manufactured by Asahi Glass Co., Ltd.), $C_4F_9OCH_3$ (Novec-7100, trade name, manufactured by 3M), $C_4F_9OC_2H_5$ (Novec-7200, trade name, manufactured by 3M), $C_6F_{13}OCH_3$ (Novec-7300, trade name, manufactured by 3M), etc.

The fluoro-alkylamine may, for example, be perfluorotripropylamine or perfluorotributylamine.

The fluoro-alcohol may, for example, be 2,2,3,3-tetrafluoropropanol, 2,2,2-trifluoroethanol or hexafluoroisopropanol.

The fluorinated organic solvent is preferably a fluoro-alkane, a fluoro-aromatic compound, a fluoro-alcohol or a fluoro-alkyl ether, particularly preferably a fluoro-alcohol or a fluoro-alkyl ether, from such a viewpoint that the present compound is thereby readily soluble.

The non-fluorinated organic solvent is preferably a compound composed solely of hydrogen atoms and carbon atoms, or a compound composed solely of hydrogen atoms, carbon atoms and oxygen atoms, and a hydrocarbon type organic solvent, an alcohol type organic solvent, a ketone type organic solvent, an etheric organic solvent, a glycol etheric organic solvent or an ester type organic solvent may be mentioned.

The hydrocarbon type organic solvent is preferably hexane, heptane, cyclohexane or the like.

The alcohol type organic solvent is preferably methanol, ethanol, propanol, isopropanol or the like.

The ketone type organic solvent is preferably acetone, methyl ethyl ketone, methyl isobutyl ketone or the like.

The etheric organic solvent is preferably diethyl ether, tetrahydrofuran, tetraethylene glycol dimethyl ether or the like.

The glycol etheric organic solvent is preferably methyl cellosolve, ethyl cellosolve, butyl cellosolve, propylene glycol monomethyl ether or the like.

The ester type organic solvent is preferably ethyl acetate, butyl acetate or the like.

The non-fluorinated organic solvent is particularly preferably a glycol ether type organic solvent or a ketone type organic solvent from the viewpoint of the solubility of the present compound.

The medium is preferably at least one type of organic solvent selected from the group consisting of a fluoroalkane, a fluoro-aromatic compound, a fluoro-alkyl ether, a fluoro-alcohol, a compound composed solely of hydrogen atoms and carbon atoms, and a compound composed solely of hydrogen atoms, carbon atoms and oxygen atoms. Particularly preferred is a fluorinated organic solvent selected from the group consisting of a fluoro-alkane, a fluoro-aromatic compound, a fluoro-alkyl ether and a fluoro-alcohol.

With a view to increasing the solubility of the present compound, it is preferred to contain, as the medium, at least one type of organic solvent selected from the group consisting of a fluoroalkane, a fluoro-aromatic compound, a fluoro-alkyl ether, a fluoro-alcohol, as fluorinated organic solvents, and a compound composed solely of hydrogen atoms, carbon atoms and oxygen atoms, as a non-fluorinated organic solvent, in a total amount of at least 90 mass % of the entire medium.

(Other Additives)

The present composition may further contain other additives as the case requires.

Such other additives may, for example, be colloidal silica, a ultraviolet absorber, a photostabilizer, a thermosetting stabilizer, an antioxidant, a leveling agent, a defoaming agent, a thickener, an antisettling agent, a pigment, a dye, a dispersant, an antistatic agent, a surfactant (an antifogging agent, a leveling agent, etc.), metal oxide particles, various resins (an epoxy resin, an unsaturated polyester resin, a polyurethane resin, etc.), etc.

Further, at the time of using the present compound, compounds inevitably included during the production the present compound (hereinafter referred to also as impurities) may be accompanied. Specifically, such impurities are by-products formed in the production step of producing the present compound and components included in the production step of producing the present compound. The content of such impurities is preferably at most 5 mass %, particularly preferably at most 2 mass %, to the present compound (100 mass %). When the content of impurities is within the above range, it is possible to impart excellent antifouling properties (oil-based ink repellency, fingerprint stain removability) to the hard coating layer.

Identification and quantitative determination of by-products in the present compound are carried out by $^1$H-NMR (300.4 MHz) and $^{19}$F-NMR (282.7 MHz).

(Composition)

The content of the present compound is preferably from 0.01 to 5 mass %, more preferably from 0.05 to 4 mass %, particularly preferably from 0.1 to 3 mass %, in the solid content (100 mass %) of the present composition. When the content of the present compound is within the above range, the storage stability of the present composition, and the appearance, abrasion resistance and antifouling properties (oil-based ink repellency, fingerprint stain removability) of the hard coating layer, will be good.

The content of the photopolymerizable compound is preferably from 20 to 98.99 mass %, more preferably from 50 to 98.99 mass %, further preferably from 60 to 98.99 mass %, particularly preferably from 80 to 98.99 mass %, in the solid content (100 mass %) of the present composition. When the content of the photopolymerizable compound is within the above range, the storage stability of the present composition, and the appearance, abrasion resistance and antifouling properties (oil-based ink repellency, fingerprint stain removability) of the hard coating layer, will be good.

The content of the photopolymerization initiator is preferably from 1 to 15 mass %, more preferably from 3 to 15 mass %, particularly preferably from 3 to 10 mass %, in the solid content (100 mass %) of the present composition. When the content of the photopolymerization initiator is within the above range, compatibility with the photopolymerizable compound will be good. Further, the curability of the present composition will be good, and the cured film thereby obtainable will be excellent in hardness.

In a case where a medium is incorporated, the content of the medium is preferably from 50 to 95 mass %, more preferably from 55 to 90 mass %, particularly preferably from 60 to 85 mass %, in the present composition (100 mass %).

In a case where other additives are incorporated, the content of such other additives is preferably from 0.5 to 20 mass %, more preferably from 1 to 15 mass %, particularly preferably from 1 to 10 mass %, in the solid content (100 mass %) of the present composition.

The solid content concentration in the present composition may be adjusted so that liquid physical properties suitable for the coating method may be thereby obtainable. The solid content concentration in the present composition is, for example, preferably from 5 to 50 mass %, more preferably from 10 to 45 mass %, particularly preferably from 15 to 40 mass %.

[Article]

The article of the present invention comprises a substrate and a hard coating layer formed from the present composition. With a view to improving the adhesion between the substrate and the hard coating layer, the article may further has a primer layer between the substrate and the hard coating layer.

From the viewpoint of abrasion resistance and antifouling properties, the thickness of the hard coating layer is preferably from 0.5 to 10 μm, particularly preferably from 1 to 5 μm.

(Substrate)

The substrate is a member constituting the main body or the surface of various articles (such as an optical lens, a display, an optical recording medium, etc.) for which abrasion resistance and antifouling properties are required.

The material for the surface of the substrate may, for example, be a metal, a resin, glass, ceramics, stone or a composite material thereof. The material for the surface of the substrate in an optical lens, a display or an optical recording medium is preferably glass or a transparent resin substrate.

The glass is preferably soda lime glass, alkali alumino silicate glass, borosilicate glass, alkali-free glass, crystal glass or quartz glass, particularly preferably chemically tempered soda lime glass, chemically tempered alkali alumino silicate glass or chemically tempered borosilicate glass. The material for the transparent resin substrate is preferably an acrylic resin or a polycarbonate resin.

By using the present composition, a hard coating layer excellent in abrasion resistance and antifouling properties (oil-based ink repellency, fingerprint stain removability) can be obtained. An article having such a hard coating layer is suitable as a member constituting a touch panel. A touch panel is an input unit of an input/display device (touch panel device) having combined a display device and a device to input a contact point information by contact with e.g. a finger. The touch panel is constituted by a substrate and, depending upon the input detection system, a transparent conductive film, electrodes, wirings, IC, etc. By using the surface having the hard coating layer, of the article, as the input surface of the touch panel, it is possible to obtain a touch panel having excellent antifouling properties (oil-based ink repellency, fingerprint stain removability). The material for the substrate for a touch panel has translucency. Specifically, the vertical incidence visible light transmittance in accordance with JIS R3106 is at least 25%.

(Primer Layer)

The primer layer may be a known one. The primer layer may, for example, be formed by applying a composition for forming a primer layer on the surface of a substrate, followed by drying.

(Method for Forming Article)

The article may be produced, for example, via the following steps (I) and (II).

(I) A step of forming a primer layer by applying a composition for forming a primer layer on the surface of a substrate, followed by drying, as the case requires.

(II) A step of forming a hard coating layer by applying the present composition on a substrate or on the surface of the primer layer to obtain a coating film and, in a case where the coating film contains a medium, removing the medium, followed by photocuring.

Step (I):

As the coating method, a known method may suitably be employed. Such a coating method may, for example, be a spin coating method, a wipe coating method, a spray coating method, a squeegee coating method, a dip coating method, a die coating method, an ink jet method, a flow coating method, a roll coating method, a casting method, a Langmuir-Blodgett method or a gravure coating method.

The temperature for drying is preferably from 50 to 140° C.

The drying time is preferably from 5 minutes to 3 hours.

Step (II):

As the coating method, the known coating method exemplified in step (I) may be mentioned.

In a case where the present composition contains a medium, the medium is removed from the coating film to form a dried film before photocuring. As the method for removing the medium, a known method may suitably be employed. Such a removal method may be a method of heating, vacuuming or heating under reduced pressure. Here, the obtained dried film contains preferably less than 10 mass %, more preferably less than 1 mass %, of the medium.

The temperature in the case of heating is preferably from 50 to 120° C.

The time for removal of the solvent is preferably from 0.5 minute to 3 hours.

The photocuring is preferably applied to the coating film when the present composition contains no medium, or to the dried coating film when the present composition contains a medium.

The photocuring is carried out by applying active energy rays.

The active energy rays may, for example, be ultraviolet rays, electron rays, X-rays, radioactive rays, high frequency radiation rays, etc., and ultraviolet rays with a wavelength of from 180 to 500 nm are economically preferred.

As an active energy ray source, an ultraviolet irradiation device (such as a xenon lamp, a low pressure mercury lamp, a high pressure mercury lamp, an ultrahigh pressure mercury lamp, a metal halide lamp, a carbon arc lamp or a tungsten lamp), an electron ray irradiation device, an X-ray irradiation device, a high frequency radiation generating device, etc. may be used.

The time for irradiation with active energy rays may be suitably selected by conditions such as the type of the present compound, the type of the photopolymerizable compound, the type of the photopolymerization initiator, the thickness of the coating film, the active energy ray source, etc. Usually, the purpose is accomplished by irradiation for from 0.1 to 60 seconds.

For the purpose of completing the curing reaction, the irradiation with active energy rays may be followed by heating. The heating temperature is preferably from 50 to 120° C.

EXAMPLES

Now, the present invention will be described in further detail with reference to Examples, but it should be understood that the present invention is by no means limited to these Examples. In the following, "%" is "mass %" unless otherwise specified. Here, Ex. 1, 2 and 5 to 7 are Examples of the present invention, and Ex. 3 and 4 are Comparative Examples.

[Measurements, Evaluations]

(Number Average Molecular Weight (Mn))

Gel permeation chromatography (GPC) of a few types of monodispersed polymethyl methacrylates different in the polymerization degree which are commercially available as standard reagents for molecular weight measurement, was measured by a commercially available measuring apparatus (apparatus name: HLC-8220GPC, manufactured by Tosoh Corporation) using, as an eluent, a mixed solvent of ASAHIKLIN AK-225 (trade name, manufactured by Asahi Glass Co., Ltd., $C_3F_5HCl_2$):hexafluoroisopropanol=99:1 (volume ratio), and a calibration curve was prepared based on the relation between the molecular weights of the polymethyl methacrylates and the retention times.

A fluorinated ether compound was diluted with the above mixed solvent to 1.0 mass % and passed through a 0.5 μm filter, whereupon with respect to the fluorinated ether compound, GPC was measured by means of the above GPC measuring apparatus.

Using the above calibration curve, the GPC spectrum of the fluorinated ether compound was subjected to a computer analysis to obtain the number average molecular weight (Mn) of the fluorinated ether compound.

(Water Contact Angle)

In accordance with JIS R3257 "Method for testing wettability of substrate glass surface", water droplets were placed at 5 positions on a hard coating layer, and with respect to each water droplet, the water contact angle was measured by a sessile drop method. The droplets were about 2 μL/droplet, and the measurement was conducted at 20° C. The water contact angle is represented by an average value (n=5) of the 5 measured values. Here, from the viewpoint of antifouling properties, the water contact angle is preferably at least 95 degrees.

(n-Hexadecane Contact Angle)

In accordance with JIS R3257 "Method for testing wettability of substrate glass surface", n-hexadecane droplets were placed at 3 positions on a hard coating layer, and with respect to each n-hexadecane droplet, the n-hexadecane contact angle was measured by a sessile drop method. The droplets were about 2 μL/droplet, and the measurement was conducted at 20° C. The contact angle is represented by an average value (n=3) of the 3 measured values. Here, from the viewpoint of antifouling properties, the n-hexadecane contact angle is preferably at least 60 degrees.

(Appearance of Hard Coating Layer)

In accordance with the following standards, the appearance of a hard coating layer was evaluated by visual observation.

○ good: No foreign matter is observed, and the film thickness is uniform.

Δ (acceptable): No foreign matter is observed, but an irregularity is observed in the film thickness.

X (no good): A foreign matter is observed, and an irregularity is observed in the film thickness.

(Oil-Based Ink Repellency)

On the surface of a hard coating layer, a line was drawn by a felt pen (trade name: Mckee Extremely Slender Black Color, manufactured by Zebra Co., Ltd.), and the attached state of the oil-based ink was visually observed and evaluated. The evaluation standards were as follows.

◉ (excellent): Oil-based ink is repelled spherically.

○ (good): Oil-based ink is repelled not spherically but linearly, and the line width is less than 50% of the width of the pen tip of the felt pen.

Δ (acceptable): Oil-based ink is repelled not spherically but linearly, and the line width is at least 50% and less than 100% of the width of the pen tip of the felt pen.

X (no good): Oil-based ink is not repelled spherically or linearly, and a line is clearly drawn on the surface.

(Fingerprint Stain Removability)

An artificial fingerprint liquid (a liquid composed of oleic acid and squalene) was deposited on a flat surface of a silicon rubber stopper, and then, excess oil was wiped off with a nonwoven fabric (trade name: BEMCOT M-3, manufactured by Asahi Kasei Corporation) to prepare a fingerprint stamp. On an article having a hard coating layer, the fingerprint stamp was placed and pressed under a load of 1 kg for 10 seconds. The haze at the portion where the fingerprint was stamped, was measured by a haze meter (manufactured by Toyo Seiki Co., Ltd.). Then, at the portion where the fingerprint was stamped, by means of a reciprocal traverse tester (manufactured by KNT) having tissue paper attached, wiping was carried out under a load of 500 g. The haze value was measured after every wiping reciprocation, whereby a case where the haze was no longer visually observed within 10 wiping reciprocations, was taken as ○ (good), and a case where the haze was visually observed till 10 wiping reciprocations, was taken as X (no good).

(Abrasion Resistance)

With respect to an article having a hard coating layer, in accordance with JIS L0849, by means of a reciprocal traverse tester (manufactured by KNT), a cellulose nonwoven fabric (trade name: KURAFLEX, manufactured by Kuraray Kuraflex Co., Ltd.) was reciprocated 5,000 times under a load of 500 g, whereupon the water contact angle and the n-hexadecane contact angle were measured.

The smaller the decrease of the water contact angle and the n-hexadecane contact angle when the number of abrasion times was increased, the smaller the decrease in the performance by abrasion, and the better the abrasion resistance.

(Pencil Hardness)

Measured in accordance with JIS K5600.

[Compounds]

(Photopolymerizable Compounds)

(a-1): dipentaerythritol hexaacrylate (corresponding to monomer (a1))

(a-2): tris(acryloyloxyethyl) isocyanurate (corresponding to monomer (a12)).

(Photopolymerization Initiator)

(b-1): 2-methyl-1-{4-(methylthio)phenyl}-2-morpholino-propan-1-one. (organic solvent)

(c-1): 2,2,3,3-tetrafluoropropanol (c-2): propylene glycol monomethyl ether (c-3): butyl acetate

[Composition for Forming Hard Coating Layer]

Into a 30 mL vial tube, 2 mg of a fluorinated ether compound produced in the following Example or a mixture containing it, 94 mg of photopolymerizable compound (a-1), 94 mg of photopolymerizable compound (a-2), 12 mg of photopolymerization initiator (b-1), 150 mg of organic solvent (c-1) and 180 mg of organic solvent (c-3) were put and stirred for 1 hour at room temperature in a light shielding condition to obtain a composition for forming a hard coating layer.

Then, on the surface of a polyethylene terephthalate (hereinafter referred to also as PET) substrate, the composition for forming a hard coating layer was applied by bar coating to form a coating film, followed by drying for one minutes on a hot plate of 50° C., to form a dried film on the surface of the substrate. Then, by means of a high pressure mercury lamp, ultraviolet rays (light quantity: 300 mJ/cm², cumulative energy of ultraviolet rays with a wavelength of 365 nm) were applied to form a hard coating layer having a thickness of 5 μm on the surface of the substrate. The composition of the composition for forming a hard coating layer and the results of evaluation of the hard coating layer are shown in Table 1.

Ex. 1: Production of Compound (1-1a-1)

Ex. 1-1

Into a 300 mL three-necked round-bottomed flask, 14.1 g of a sodium borohydride powder was put, and 350 g of ASAHIKLIN AK-225 was added. While cooling and stirring in an ice bath, a solution having 100 g of compound (12a), 15.8 g of methanol and 22 g of ASAHIKLIN AK-225 mixed, was slowly dropwise added from a dropping funnel in a nitrogen atmosphere so that the internal temperature would not exceed 10° C. After dropwise addition of the entire amount, a solution having 10 g of methanol and 10 g of ASAHIKLIN AK-225 mixed, was dropwise added. Then, the ice bath was removed, and while raising the temperature slowly to room temperature, stirring was continued. After stirring at room temperature for 12 hours, the reaction mixture was cooled again in an ice bath, and an aqueous hydrochloric acid solution was dropwise added until the liquid became acidic. After termination of the reaction, the reaction mixture was washed once with water and once with a saturated aqueous sodium chloride solution, whereupon an organic phase was recovered. The recovered organic phase was dried over magnesium sulfate, and then, the solid content was filtered off, and the filtrate was concentrated by an evaporator. The recovered concentrated liquid was distilled under reduced pressure to obtain 80.6 g (yield: 88%) of compound (11a).

$$CF_2=CFO-CF_2CF_2CF_2C(=O)OCH_3 \quad (12a)$$

$$CF_2=CFO-CF_2CF_2CF_2CH_2OH \quad (11a)$$

NMR spectrum of compound (11a):

¹H-NMR (300.4 MHz, solvent: deuterated chloroform, standard: TMS) δ (ppm): 2.2 (1H), 4.1 (2H)

¹⁹F-NMR (282.7 MHz, solvent: deuterated chloroform, standard: CFCl₃) δ (ppm): −85.6 (2F), −114.0 (1F), −122.2 (1F), −123.3 (2F), −127.4 (2F), −135.2 (1F)

Ex. 1-2

Into a 50 mL eggplant flask connected to a reflux condenser, 5.01 g of compound (11a) obtained in Ex. 1-1 and 5.06 g of methanol were introduced, and 0.54 g of pellets of potassium hydroxide were added. After stirring in a nitrogen atmosphere at 25° C. overnight, an aqueous hydrochloric acid solution was added to treat excess potassium hydroxide, and water and ASAHIKLIN AK-225 were added to carry out liquid separation treatment. After washing with water three times, the organic phase was recovered and concentrated by an evaporator to obtain 5.14 g of a methanol adduct. Again into a 50 mL eggplant flask connected to a reflux condenser, 1.0 g of the methanol adduct and 0.13 g of pellets of potassium hydroxide were added, and while heating at 100° C., 10.86 g of compound (11a) was dropwise added. While maintaining 100° C., stirring was further continued for 9 hours, whereupon an aqueous hydrochloric acid solution was added to treat excess potassium hydroxide, and water and ASAHIKLIN AK-225 were added to carry out liquid separation treatment. After washing with water three times, the organic phase was recovered and concentrated by an evaporator to obtain 11 g of a highly viscous oligomer. It was again diluted by two times with ASAHIKLIN AK-225 and developed and fractionated by silica gel column chromatography (developing solvent: ASAHIKLIN AK-225). With respect to each fraction, an average value of the number of units (n+1) was obtained from the integrated value of $^{19}$F-NMR. 4.76 g of compound (10a-1) having fractions with an average value of (n+1) in the following formula (10a-1) being from 7 to 10 put together, was obtained.

$$CH_3-O-(CF_2CFHO-CF_2CF_2CF_2CH_2O)_{n+1}-H \qquad (10a\text{-}1)$$

NMR Spectrum of Compound (10a-1):
$^1$H-NMR (300.4 MHz, solvent: deuterated chloroform, standard: TMS) δ (ppm): 3.7 (3H), 4.0 (2H), 4.4 (18.4H), 6.0 to 6.2 (9.2H)
$^{19}$F-NMR (282.7 MHz, solvent: deuterated chloroform, standard: CFCl$_3$) δ (ppm): −84.7 to −87.0 (18.4F), −89.4 to −91.6 (18.4F), −121.5 (16.4F), −123.4 (2F), −128.0 (18.4F), −145.3 (9.2F)
Average value of the number of units (n+1): 9.2

Ex. 1-3

Into a 200 mL eggplant flask connected to a reflux condenser, 100 g of compound (10a-1) obtained in Ex. 1-2 was added, and while stirring in a nitrogen atmosphere at room temperature, 28.6 g of acetyl chloride was dropwise added over a period of 20 minutes. After stirring at 50° C. for 4.5 hours, disappearance of the raw material was confirmed by $^1$H-NMR. The reaction solution was concentrated by an evaporator. The solution after concentration was diluted with ASAHIKLIN AK-225 and treated with 20 g of silica gel, whereupon solids were removed by filtration. The solution was concentrated again by an evaporator to obtain 98.1 g (yield: 97%) of compound (9a-1) having an average value of the number of units (n+1) in the following formula (9a-1) being 9.2.

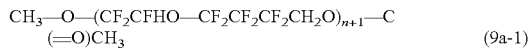

$$CH_3-O-(CF_2CFHO-CF_2CF_2CF_2CH_2O)_{n+1}-C(=O)CH_3 \qquad (9a\text{-}1)$$

NMR Spectrum of Compound (9a-1):
$^1$H-NMR (300.4 MHz, solvent: deuterated chloroform+R-113 (CCl$_2$FCClF$_2$), standard: TMS) δ (ppm): 2.0 (3H), 3.6 (3H), 4.4 to 4.9 (18.4H), 6.0 to 6.2 (9.2H)
$^{19}$F-NMR (282.7 MHz, solvent: deuterated chloroform+R-113, standard: CFCl$_3$) δ (ppm): −85.5 to −86.7 (18.4F), −91.5 to −93.9 (18.4F), −121.7 to −122.8 (18.4F), −128.4 to −129.6 (18.4F), −145.9 (9.2F)
Average value of the number of units (n+1): 9.2

Ex. 1-4

An autoclave (made of nickel, internal capacity: 1 L) was provided, and at a gas discharge outlet of the autoclave, a condenser held at 25° C., a NaF pellets-packed layer and a condenser held at 0° C. were set in series. Further, a liquid-returning line to return a liquid condensed from the condenser held at 0° C. to the autoclave, was set.

Into the autoclave, 750 g of R-419 (CF$_2$C$_1$CFClCF$_2$OCF$_2$CF$_2$Cl)) was put and stirred while maintaining the temperature at 25° C. After blowing nitrogen gas at 25° C. for one hour into the autoclave, fluorine gas diluted to 20 vol % with nitrogen gas (hereinafter referred to also as the 20% fluorine gas), was blown into it at 25° C. for one hour at a flow rate of 5.3 L/hr. Then, while blowing the 20% fluorine gas at the same flow rate, a solution having 70 g of the compound (9a-1) obtained in Ex. 1-3 dissolved in 136 g of R-419, was injected into the autoclave over a period of 7.4 hours.

Then, while blowing the 20% fluorine gas at the same flow rate, the internal pressure of the autoclave was raised to 0.15 MPa (gauge pressure). Into the autoclave, 4 mL of a benzene solution containing 0.056 g/mL of benzene in R-419, was injected while heating to from 25° C. to 40° C., whereupon the benzene solution injection inlet of the autoclave was closed. After stirring for 20 minutes, 4 mL of the benzene solution was injected again while maintaining the temperature at 40° C., whereupon the injection inlet was closed. The same operation was further repeated 4 times. The total injected amount of benzene was 0.1 g.

Further, stirring was continued for one hour while blowing the 20% fluorine gas at the same flow rate. Then, the internal pressure of the autoclave was adjusted to the atmospheric pressure, and nitrogen gas was injected for one hour. The content in the autoclave was concentrated by an evaporator to obtain 82.3 g (yield: 97%) of compound (7a-1) of the following formula (7a-1) wherein the average value of the number of units (n) is 8.2.

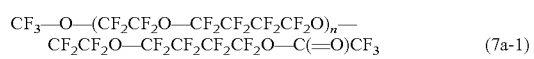

$$CF_3-O-(CF_2CF_2O-CF_2CF_2CF_2CF_2O)_n-CF_2CF_2O-CF_2CF_2CF_2O-C(=O)CF_3 \qquad (7a\text{-}1)$$

NMR Spectrum of Compound (7a-1):
$^{19}$F-NMR (282.7 MHz, solvent: deuterated chloroform+R-113, standard:CFCl$_3$) δ (ppm): −57.3 (3F), −77.5 (3F), −85.0 (34.8F), −88.5 (2F), −90.5 (34.8F), −92.5 (2F), −127.5 (36.8F)
Average value of the number of units (n): 8.2

Ex. 1-5

Into a 500 mL round-bottomed eggplant flask made of a tetrafluoroethylene/perfluoro(alkoxy vinyl ether) copolymer (PFA), 82.3 g of the compound (7a-1) obtained in Ex. 1-4 and 250 mL of ASAHIKLIN AK-225 were put. In a nitrogen atmosphere, 3.9 g of methanol was slowly dropwise added from a dropping funnel. Stirring was continued for 12 hours. The reaction mixture was concentrated by an evaporator to obtain 77.7 g (yield: 100%) of compound (6a-1) of the following formula (6a-1) wherein the average value of the number of units (n) is 8.2.

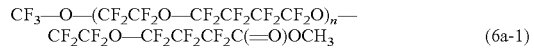

$$CF_3-O-(CF_2CF_2O-CF_2CF_2CF_2CF_2O)_n-CF_2CF_2O-CF_2CF_2CF_2C(=O)OCH_3 \qquad (6a\text{-}1)$$

NMR Spectrum of Precursor (6a-1):
$^1$H-NMR (300.4 MHz, solvent: deuterated chloroform+R-113, standard: TMS) δ (ppm): 3.8 (3H)
$^{19}$F-NMR (282.7 MHz, solvent: deuterated chloroform+R-113, standard: CFCl$_3$) δ (ppm): −57.3 (3F), −84.9 (34.8F), −90.5 (34.8F), −92.5 (2F), −120.2 (2F), −127.3 (32.8F), 128.2 (2F)
Average value of the number of units (n): 8.2

Ex. 1-6

Into a 500 mL round-bottomed eggplant flask made of glass, 0.52 g of lithium chloride, 77.7 g of the compound (6a-1) obtained in Ex. 1-5 and 51.6 mg of dehydrated ethanol were put. While stirring the obtained mixed solution at 10° C., a solution having 2.11 g of sodium borohydride dissolved in 63.3 g of dehydrated ethanol, was dropwise added over a period of 30 minutes. After stirring for 18 hours, 10% hydrochloric acid was added until the solution became acidic. The obtained solution was diluted with 100 mL of ASAHIKLIN AK-225 and then washed twice with 100 mL of water. The organic phase was recovered and concentrated by an evaporator, followed by vacuum drying to obtain 74.9 g (yield: 97.3%) of compound (5a-1) of the following formula (5a-1) wherein the average value of the number of units (n) is 8.2.

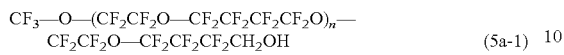
(5a-1)

NMR Spectrum of Precursor (5a-1):

$^1$H-NMR (300.4 MHz, solvent: deuterated chloroform+R-113, standard: TMS) δ (ppm): 4.0 (2H), 2.8 (1H)

$^{19}$F-NMR (282.7 MHz, solvent: deuterated chloroform+R-113, standard: CFCl$_3$) δ (ppm): −57.1 (3F), −84.9 (34.8F), −90.0 (34.8F), −92.1 (2F), −124.4 (2F), −127.2 (32.8F), 128.6 (2F)

Average value of the number of units (n): 8.2

Ex. 1-7

Into a 200 mL round-bottomed eggplant flask made of glass, 37 g of the compound (5a-1) obtained in Ex. 1-6, 100 mL of ASAHIKLIN AK-225, 1.68 g of triethylamine and about 1 mg of Q-1301 (trade name, manufactured by Wako Pure Chemical Industries, Ltd.) were added. While stirring the obtained solution, 1.49 g of methacrylic acid chloride was dropwise added. After stirring at room temperature for 4 hours, the progress of the reaction was traced by $^1$H-NMR, whereby a residue of compound (5a-1) was confirmed, and therefore, 0.5 g of triethylamine and 0.5 g of methacrylic acid chloride were added. After stirring further at room temperature for 16 hours, the progress of the reaction was traced by $^1$H-NMR, whereby compound (5a-1) was found to have been all consumed. 50 mL of water was added to the solution, and the organic phase was separated. By washing twice with 50 mL of a saturated sodium hydrogen carbonate aqueous solution and once with 50 mL of a saturated sodium chloride aqueous solution, the organic phase was recovered. The recovered organic phase was dried over magnesium sulfate, and then, the solid content was filtered off, followed by concentration by an evaporator to obtain 36.4 g (yield: 94.9%) of compound (1-1a-1). The number average molecular weight was 2,837.

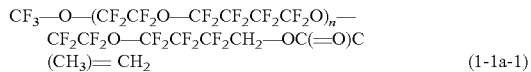
(1-1a-1)

NMR Spectrum of Precursor (1-1a-1):

$^1$H-NMR (300.4 MHz, solvent: deuterated chloroform+R-113, standard: TMS) δ (ppm): 6.2 (1H), 5.6 (1H), 4.5 (2H), 2.0 (3H)

$^{19}$F-NMR (282.7 MHz, solvent: deuterated chloroform+R-113, standard: CFCl$_3$) δ (ppm): −57.3 (3F), −84.9 (34.8F), −90.0 (34.8F), −92.2 (2F), −121.4 (2F), −127.4 (32.8F), 128.5 (2F)

Average value of the number of units (n): 8.2

Ex. 2: Production of Compound (1-6a-1), and Formation of Hard Coating Layer

Ex. 2-1

Into a 2 L three necked flask equipped with a dropping funnel, a condenser, a thermometer and a stirrer, 1.0 g of a cyclic trimer of hexamethylene diisocyanate (trade name: DURANATE THA-100, manufactured by Asahi Kasei Chemicals Corporation) and 2.9 g of ASAHIKLIN AK-225 were put, and 7.5 mg of dibutyltin dilaurate (extra pure reagent, manufactured by Wako Pure Chemical Industries, Ltd.) was added. While stirring in air at room temperature, a solution having 2.0 g of compound (5a-1) obtained in Ex. 1-6 dissolved in 2.9 g of ASAHIKLIN AK-225, was dropwise added over a period of 50 minutes, followed by stirring at room temperature for 12 hours. The reaction solution was heated to 45° C., and 0.76 g of hydroxyethyl acrylate was dropwise added in 2 minutes, followed by stirring for 3 hours. By the infrared absorption spectrum, it was confirmed that absorption by an isocyanate group disappeared completely, and therefore, 5.0 g of hexane was added to the obtained reaction solution, and the supernatant was separated. 0.4 mg of phenothiazine and 9 g of acetone were added and stirred for 5 minutes, followed by concentration by an evaporator, to obtain 2.0 g of a mixture of compound (1-6a-1) of the following formula (13) wherein one of $G^1$ to $G^3$ is a group represented by the following formula (14), the rest being groups represented by the following formula (15), a compound of the formula (13) wherein two among $G^1$ to $G^3$ are groups represented by the following formula (14) and the rest being a group represented by the following formula (15), a compound of the formula (13) wherein all of $G^1$ to $G^3$ are groups represented by the following formula (14), and a compound of the formula (13) wherein all of $G^1$ to $G^3$ are groups represented by the following formula (15). The number average molecular weight (Mn) of the mixture was 928, and the number average molecular weight (Mn) of compound (1-6a-1) was 3,417.

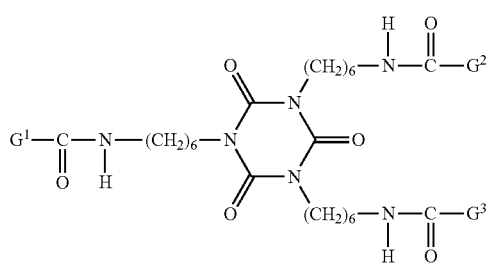
(13)

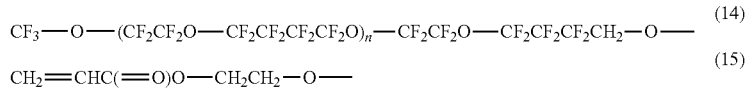

$$CF_3-O-(CF_2CF_2O-CF_2CF_2CF_2CF_2O)_n-CF_2CF_2O-CF_2CF_2CF_2CH_2-O- \quad (14)$$

$$CH_2=CHC(=O)O-CH_2CH_2-O- \quad (15)$$

Ex. 2-2

Using the mixture containing compound (1-6a-1), a composition (2) for forming a hard coating layer was obtained, and a hard coating layer was formed. The evaluation results are shown in Table 1.

Ex. 3: Production of Compound (16), and Formation of Hard Coating Layer

Ex. 3-1

In accordance with the method disclosed in Example 1 of Patent Document 2, a fluorinated compound having an acryloyloxy group at each terminal of a poly(oxyperfluoroalkylene) chain, composed of a combination of ($CF_2O$) and ($CF_2CF_2O$), was copolymerized with hydroxyethyl methacrylate, and then reacted with 2-acryloyloxyethyl isocyanate to obtain compound (16) (number average molecular weight (Mn): 2,400).

Ex. 3-2

Using compound (16) produced in Ex. 3-1, a composition (3) for forming a hard coating layer was obtained, and a hard coating layer was formed. The evaluation results are shown in Table 1.

Ex. 4: Production of Compound (1-6a-4), and Formation of Hard Coating Layer

Ex. 4-1

In accordance with the method disclosed in Examples 2 and 3 of Patent Document 1, a mixture of compound (1-6a-4) of the formula (13) wherein one of $G^1$ to $G^3$ is a group represented by the following formula (14-2) and the rest being groups represented by the formula (15), a compound of the formula (13) wherein two among $G^1$ to $G^3$ are groups represented by the following formula (14-2) and the rest being a group represented by the formula (15), a compound of the formula (13) wherein all of $G^1$ to $G^3$ are groups represented by the following formula (14-2), and a compound of the formula (13) wherein all of $G^1$ to $G^3$ are groups represented by the formula (15), was synthesized. The number average molecular weight (Mn) of the mixture was 1,159, and the number average molecular weight (Mn) of compound (1-6a-4) was 3,160.

$$CF_3CF_2-O-(CF_2CF_2CF_2O)_n-CF_2CF_2CH_2-O- \quad (14\text{-}2)$$

Ex. 4-2

Using the mixture containing compound (1-6a-4) produced in Ex. 4-1, a composition (4) for forming a hard coating layer was obtained, and a hard coating layer was formed. The evaluation results are shown in Table 1.

Ex. 5: Production of Compound (18), and Formation of Hard Coating Layer

Ex. 5-1

Using compound (5a-1) obtained in Ex. 1-6, in accordance with the method disclosed in Paragraph [0140] of Japanese Patent No. 4,923,572, a compound (compound (18)) represented by the following formula (18) was synthesized (number average molecular weight (Mn): 3,826).

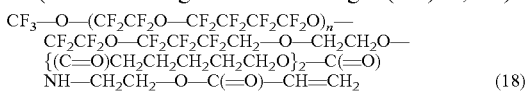

$$NH-CH_2CH_2-O-C(=O)-CH=CH_2 \quad (18)$$

Average value of the number of units (n): 5.2

Ex. 5-2

Using compound (18) produced in Ex. 5-1, a composition (5) for forming a hard coating layer was obtained, and a hard coating layer was formed. The evaluation results are shown in Table 1.

Ex. 6: Production of Mixture Containing Compound (1-6a-2), and Formation of Hard Coating Layer

Ex. 6-1

In the same manner as in Ex. 2-1 except that instead of compound (5a-1), compound (5a-2) wherein the average value of the number of units (n) is 6 was used, a mixture of compound (1-6a-2) of the formula (13) wherein one of $G^1$ to $G^3$ is a group represented by the formula (14) and the rest being groups represented by the formula (15), a compound of the formula (13) wherein two among $G^1$ to $G^3$ are groups represented by the formula (14) and the rest being a group represented by the formula (15), a compound of the formula (13) wherein all of $G^1$ to $G^3$ are groups represented by the formula (14), and a compound of the formula (13) wherein all of $G^1$ to $G^3$ are groups represented by the formula (15), was obtained. The number average molecular weight (Mn) of the mixture was 842, and the number average molecular weight (Mn) of compound (1-6a-2) was 2,740.

Ex. 6-2

Using the mixture containing compound (1-6a-2) produced in Ex. 6-1, a composition (6) for forming a hard coating layer was obtained, and a hard coating layer was formed. The evaluation results are shown in Table 1.

Ex. 7: Production of Mixture Containing Compound (1-6a-3), and Formation of Hard Coating Layer

Ex. 7-1

In the same manner as in Ex. 2-1 except that instead of compound (5a-1), compound (5a-3) wherein the average value of the number of units (n) is 15 was used, a mixture of compound (1-6a-3) of the formula (13) wherein one of $G^1$ to $G^3$ is a group represented by the formula (14) and the rest being groups represented by the formula (15), a compound of the formula (13) wherein two among $G^1$ to $G^3$ are groups represented by the formula (14) and the rest being a group represented by the formula (15), a compound of the formula (13) wherein all of $G^1$ to $G^3$ are groups represented by the formula (14), and a compound of the formula (13) wherein all of $G^1$ to $G^3$ are groups represented by the formula (15), was obtained. The number average molecular weight (Mn) of the mixture was 1,254, and the number average molecular weight (Mn) of compound (1-6a-3) was 5,710.

Ex. 7-2

Except that 1 mg of the mixture containing compound (1-6a-3) produced in Ex. 7-1 was used, a composition (7) for forming a hard coating layer having the same composition as the above composition for forming a hard coating layer, was obtained, and a hard coating layer was formed. The evaluation results are shown in Table 1.

(such as $[CF_2CF_2CF_2CF_2O]$) and neither terminal of the poly(oxyperfluoroalkylene) chain had a perfluoroalkylene group.

The hard coating layer in Ex. 4 was inadequate in each of the water contact angle and n-hexadecane contact angle after the abrasion resistance test. The reason is considered to be such that the poly(oxyperfluoroalkylene) chain had only a single type of oxyperfluoroalkylene groups.

INDUSTRIAL APPLICABILITY

The fluorinated ether compound of the present invention is useful to impart excellent antifouling properties (oil-based ink repellency, fingerprint stain removability) to an object (such as a hard coating layer). Further, it may be used, as mixed to a resin material, for applications to impart antifouling properties (oil-based ink repellency, fingerprint stain removability) to molded products, as a mold release agent for e.g. molds, for oil leakage prevention for e.g. bearings, for adhesion prevention of a process solution at the time of processing e.g. electronic components, for moisture prevention for processed products, etc.

TABLE 1

| | | | Ex. 2 | Ex. 3 | Ex. 4 | Ex. 5 | Ex. 6 | Ex. 7 |
|---|---|---|---|---|---|---|---|---|
| Fluorinated ether compound, mixture | | | Mixture containing (1-6a-1) | Compound (16) | Mixture containing (1-6a-4) | Compound (18) | Mixture containing (1-6a-2) | Mixture containing (1-6a-3) |
| Number average molecular weight | | | 928 | 2,400 | 1,159 | 3,826 | 842 | 1,254 |
| Composition for forming hard coating layer | | | Composition (2) | Composition (3) | Composition (4) | Composition (5) | Composition (6) | Composition (7) |
| Proportion (%) in solid content (100%) | Fluorinated ether compound, mixture | Mixture containing (1-6a-1) | 1 | — | — | — | — | — |
| | | Compound (16) | — | 1 | — | — | — | — |
| | | Mixture containing (1-6a-4) | — | — | 1 | — | — | — |
| | | Compound (18) | — | — | — | 1 | — | — |
| | | Mixture containing (1-6a-2) | — | — | — | — | 1 | — |
| | | Mixture containing (1-6a-3) | — | — | — | — | — | 0.5 |
| Composition for forming hard coating layer | | | | | | | | |
| Proportion (%) in solid content (100%) | Photopolymerizable compound | (a-1) | 46.5 | 46.5 | 46.5 | 46.5 | 46.5 | 46.8 |
| | | (a-2) | 46.5 | 46.5 | 46.5 | 46.5 | 46.5 | 46.8 |
| | Photopolymerizable initiator | (b-1) | 5.9 | 5.9 | 5.9 | 5.9 | 5.9 | 6 |
| Portion (%) in composition (100%) | Organic solvent | (c-1) | 23 | 23 | 23 | 23 | 23 | 23 |
| | | (c-2) | 18 | 18 | 18 | 18 | 18 | 18 |
| | | (c-3) | 28 | 28 | 28 | 28 | 28 | 28 |
| Evaluation | Water contact angle (degrees) | | 104.8 | 101 | 102.5 | 103.2 | 104 | 106.4 |
| | n-Hexadecane contact angle (degrees) | | 63.5 | 54.3 | 71 | 65.8 | 63.1 | 67.8 |
| | Appearance of hard coating layer | | ◯ | ◯ | ◯ | ◯ | ◯ | ◯ |
| | Oil-based ink repellency | | ◯ | Δ | ◯ | ◯ | ◯ | ◯ |
| | Fingerprint stain removability | | ◯ | Δ | ◯ | ◯ | ◯ | ◯ |
| | Pencil hardness | | 3H | 2H | 3H | 3H | 3H | 3H |
| Abrasion resistance | Water contact angle (degrees) | | 95.6 | 89.8 | 76.9 | 97.3 | 99.9 | 92.2 |
| | n-Hexadecane contact angle (degrees) | | 57.9 | 45.8 | 44.3 | 55 | 59.7 | 55.6 |

The hard coating layers in Ex. 2 and 5 to 7 formed by using the present compounds were good with respect to antifouling properties (oil-based ink repellency, fingerprint stain removability), appearance and abrasion resistance.

The hard coating layer in Ex. 3 formed by using a conventional fluorinated ether compound was inadequate in the water contact angle, n-hexadecane contact angle and oil-based ink repellency. The reason is considered to be such that the poly(oxyperfluoroalkylene) chain did not have a perfluoroalkylene group having at least 3 carbon atoms This application is a continuation of PCT Application No. PCT/JP2014/055498, filed on Mar. 4, 2014, which is based upon and claims the benefit of priority from Japanese Patent Application No. 2013-043215 filed on Mar. 5, 2013 and Japanese Patent Application No. 2013-043216 filed on Mar. 5, 2013. The contents of those applications are incorporated herein by reference in their entireties.

What is claimed is:

1. A fluorinated ether compound comprising:
  a poly(oxyperfluoroalkylene) chain having a repeated unit that comprises an oxyperfluorodimethylene group and an oxyperfluorotetramethylene group, bonded to each other, a linking group bonded to a first terminal of the poly(oxyperfluoroalkylene) chain, and at least one (meth)acryloyl group bonded to the linking group.

2. The fluorinated ether compound according to claim 1, wherein at a second terminal of the poly(oxyperfluoroalkylene) chain is bonded when the second terminal atom is a carbon atom, or a perfluoroalkyl group is bonded when the second terminal atom is an oxygen atom.

3. The fluorinated ether compound according to claim 2, wherein the second terminal of the poly(oxyperfluoroalkylene) chain is at a side where a $C_2$ oxyperfluoroalkylene group is present.

4. The fluorinated ether compound according to claim 1, which has a number average molecular weight of from 2,000 to 40,000.

5. A fluorinated ether compound represented by the following formula (1):

$$A-O-[R^{f1}O-R^{f2}O]_n-B \qquad (1),$$

wherein:

n is an integer of at least 2, $R^{f1}$ is a perfluorodimethylene group, $R^{f2}$ is a perfluorotetramethylene, A is a $C_{1-6}$ perfluoroalkyl group, a $C_{2-6}$ perfluoroalkyl group having an etheric oxygen atom, or B, B is a group represented by the following formula (2):

$$-R^{f3}(CX_2)_{m1}-Y^1-Q-[Y^2C(=O)C(R)=CH_2]_{m2} \qquad (2),$$

wherein:

$R^{f3}$ is a $C_{1-20}$ perfluoroalkylene group which optionally has an etheric oxygen atom between carbon atoms, X is a hydrogen atom or a fluorine atom, m1 is 0 or 1, $Y^1$ is a single bond, —C(=O)NH—, wherein Q is bonded to N, —OC(=O)NH—, wherein Q is bonded to N, —O—, —C(=O)O—, wherein Q is bonded to O, —OC(=O)O—, —NHC(=O)NH— or —NHC(=O)O—, wherein Q is bonded to O, Q is a single bond or a m2+1 valent organic group, $Y^2$ is —O—, —NH— or —NHC(=O)O—$(C_kH_{2k})$—O—, wherein k is an integer of from 1 to 10, and Q is bonded to N, R is a hydrogen atom or a methyl group, m2 is an integer of at least 1, wherein, when m1 is 0, $Y^1$ is not —O—, —OC(=O)NH— or —OC(=O)—, when $Y^1$ is —C(=O)NH—, —OC(=O)NH—, —O—, —C(=O)O—, —OC(=O)O—, —NHC(=O)NH— or —NHC(=O)O—, Q is a m2+1 valent organic group, and when each of $Y^1$ and $Y^2$ is —O—, Q is not a single bond.

6. The fluorinated ether compound according to claim 5, wherein the B is —$CF_2CF_2OCF_2CF_2CF_2CH_2$—OC(=O)C(R)=$CH_2$.

7. The fluorinated ether compound according to claim 5, wherein the B is —$CF_2CF_2OCF_2CF_2CF_2CH_2$—O—C(=O)NH-Q-[NHC(=O)O—$(C_kH_{2k})$—O—C(=O)C(R)=$CH_2]_{m2}$, wherein m2 is 1 or 2, provided that when m2 is 1, Q is a bivalent group obtained by removing two isocyanate groups from a diisocyante compound, and when m2 is 2, Q is a trivalent group obtained by removing three isocyanate groups from a triisocyanate compound, and k is an integer of from 2 to 6.

8. A composition for forming a hard coating layer, comprising the fluorinated ether compound of claim 1, a photopolymerizable compound that does not comprise the fluorinated ether compound, and a photopolymerization initiator.

9. The composition for forming a hard coating layer according to claim 8, wherein a content of the fluorinated ether compound is from 0.01 to 5 mass %, based on 100 mass % of a solid content.

10. The composition for forming a hard coating layer according to claim 8, further comprising a medium.

11. A composition for forming a hard coating layer, comprising the fluorinated ether compound of claim 5, a photopolymerizable compound that does not comprise the fluorinated ether compound, and a photopolymerization initiator.

12. The composition for forming a hard coating layer according to claim 11, wherein a content of the fluorinated ether compound is from 0.01 to 5 mass %, based on 100 mass % of a solid content.

13. The composition for forming a hard coating layer according to claim 11, further comprising a medium.

14. An article comprising a substrate and a hard coating layer formed from the composition of claim 8.

15. The article according to claim 14, wherein the substrate comprises a metal, a resin, glass, ceramics or a composite material thereof.

16. An article comprising a substrate and a hard coating layer formed from the composition of claim 11.

17. The article according to claim 16, wherein the substrate comprises a metal, a resin, glass, ceramics or a composite material thereof.

* * * * *